US012797564B2

(12) United States Patent
Hudson et al.

(10) Patent No.: US 12,797,564 B2
(45) **Date of Patent: *Nov. 17, 2026**

(54) SYSTEMS AND METHODS FOR SETUP OF CPAP SYSTEMS

(71) Applicant: ResMed Inc., San Diego, CA (US)

(72) Inventors: Robert Hudson, Bella Vista (AU); Kristina Zlomislic, Sydney (AU); Peter Dassos, Sydney (AU); Clare Donker, Sydney (AU); Chinmayee Somaiya, Sydney (AU); Ben Dwyer, Sydney (AU); Maria Jolliff, San Diego, CA (US); Ryan Hernandez, San Diego, CA (US); Brian Hickey, San Diego, CA (US)

(73) Assignee: ResMed Inc., San Diego, CA (US)

( * ) Notice: Subject to any disclaimer, the term of this patent is extended or adjusted under 35 U.S.C. 154(b) by 535 days.

This patent is subject to a terminal disclaimer.

(21) Appl. No.: 18/509,705

(22) Filed: Nov. 15, 2023

(65) Prior Publication Data

US 2024/0082516 A1 Mar. 14, 2024

Related U.S. Application Data

(63) Continuation of application No. 17/653,367, filed on Mar. 3, 2022, now Pat. No. 11,819,595, which is a (Continued)

(51) Int. Cl.
*A61M 16/00* (2006.01)
*A61M 16/06* (2006.01)

(52) U.S. Cl.
CPC .... *A61M 16/0003* (2014.02); *A61M 16/0066* (2013.01); *A61M 16/024* (2017.08); (Continued)

(58) Field of Classification Search
CPC .......... A61M 16/0003; A61M 16/0066; A61M 16/024; A61M 16/06; A61M 2205/3334; (Continued)

(56) References Cited

U.S. PATENT DOCUMENTS 4,944,310 A 7/1990 Sullivan
5,117,819 A 6/1992 Servidio
(Continued)

FOREIGN PATENT DOCUMENTS

CN 202365778 8/2012
DE 102014012792 3/2016
(Continued)

OTHER PUBLICATIONS

Written Opinion for International Application No. PCT/IB2019/059057, six pages, mailed Jan. 24, 2020.
(Continued)

*Primary Examiner* — Victoria Murphy
(74) *Attorney, Agent, or Firm* — Nixon & Vanderhye, PC

(57) ABSTRACT

A system for providing continuous positive air pressure therapy is provided. The system includes a patient interface, a flow generator, a sensor, and a computing device. Wireless transceivers allow wireless communication between the computing device and the flow generator and/or patient interface. Sensor data is communicated to the computing device and a leak determination is made by the computing device based on the sensor data. If a leak is detected, then troubleshooting options for correcting the leak are displayed to the patient on a display of the computing device. The troubleshooting options may be selected based on the sensed data, the type of patient interface, the type of flow generator, or characteristics of the patient using the device.

20 Claims, 15 Drawing Sheets

Related U.S. Application Data continuation of application No. 16/661,250, filed on Oct. 23, 2019, now Pat. No. 11,298,480.

(60) Provisional application No. 62/749,430, filed on Oct. 23, 2018.

(52) U.S. Cl.
CPC ..... *A61M 16/06* (2013.01); *A61M 2205/3334* (2013.01); *A61M 2205/3576* (2013.01); *A61M 2205/502* (2013.01)

(58) Field of Classification Search
CPC .... A61M 2205/3576; A61M 2205/502; A61M 16/16; A61M 2016/0027; A61M 2016/003; A61M 2205/581; A61M 2205/583; A61M 2205/6018; A61M 2205/15; A61M 2205/3553; A61M 2205/3569; A61M 2205/3584; A61M 2205/3592; A61M 2205/505; A61M 2205/6054; A61M 2205/702; A61M 16/00; A61M 16/022; A61M 2205/3561; A61M 2205/58; A61M 2205/6072; A61M 2205/70; A61M 16/0069; G16H 20/40; G16H 40/60
See application file for complete search history.

(56) References Cited

U.S. PATENT DOCUMENTS

| | | | | |
|---|---|---|---|---|
| 5,199,424 | A | 4/1993 | Sullivan et al. | |
| 5,245,995 | A | 9/1993 | Sullivan et al. | |
| 5,485,851 | A | 1/1996 | Erickson | |
| 5,503,146 | A | 4/1996 | Froehlich | |
| 5,522,382 | A | 6/1996 | Sullivan et al. | |
| 5,535,738 | A | 7/1996 | Estes | |
| 5,704,345 | A | 1/1998 | Berthon-Jones | |
| 5,823,187 | A | 10/1998 | Estes et al. | |
| 5,944,680 | A | 8/1999 | Christopherson et al. | |
| 5,947,115 | A | 9/1999 | Lordo et al. | |
| 6,029,665 | A | 2/2000 | Berthon-Jones | |
| 6,112,746 | A | 9/2000 | Kwok et al. | |
| 6,138,675 | A | 10/2000 | Berthon-Jones | |
| 6,349,724 | B1 | 2/2002 | Burton | |
| 6,357,441 | B1 | 3/2002 | Kwok et al. | |
| 6,363,933 | B1 | 4/2002 | Berthon-Jones | |
| 6,397,845 | B1 | 6/2002 | Burton | |
| 6,398,739 | B1 | 6/2002 | Sullivan et al. | |
| 6,401,713 | B1 | 6/2002 | Hill | |
| 6,546,930 | B1 | 4/2003 | Emerson et al. | |
| 6,581,602 | B2 | 6/2003 | Kwok et al. | |
| 6,634,358 | B2 | 10/2003 | Kwok et al. | |
| 6,635,021 | B1 | 10/2003 | Sullivan et al. | |
| 6,641,542 | B2 | 11/2003 | Cho et al. | |
| 6,949,073 | B2 | 9/2005 | Sarel | |
| 7,011,087 | B1 | 3/2006 | Sullivan | |
| 7,089,936 | B2 | 8/2006 | Madaus et al. | |
| 7,225,809 | B1 | 6/2007 | Bowen | |
| 7,252,640 | B2 | 8/2007 | Ni et al. | |
| 7,607,432 | B2 | 10/2009 | Sullivan | |
| 7,640,055 | B2 | 12/2009 | Geva et al. | |
| 7,717,112 | B2 | 5/2010 | Sun et al. | |
| 7,806,831 | B2 | 10/2010 | Lavie et al. | |
| 7,890,342 | B1 | 2/2011 | Yruko | |
| 7,942,824 | B1 | 5/2011 | Kayyali et al. | |
| 8,281,787 | B2 | 10/2012 | Burton | |
| 8,528,551 | B2 | 9/2013 | Mulcahy et al. | |
| 8,881,727 | B2 | 11/2014 | Aloia et al. | |
| 9,440,037 | B2 | 9/2016 | Mulcahy et al. | |
| 9,662,464 | B2 | 5/2017 | Shelly et al. | |
| 10,463,820 | B2 | 11/2019 | Mulcahy et al. | |
| 2003/0097125 | A1 | 5/2003 | Hall | |
| 2003/0236450 | A1 | 12/2003 | Kocinski et al. | |
| 2004/0065330 | A1 | 4/2004 | Landis | |
| 2004/0187871 | A1 | 9/2004 | Kimmel | |
| 2005/0005937 | A1 | 1/2005 | Farrugia | |
| 2005/0016534 | A1 | 1/2005 | Ost | |
| 2005/0038353 | A1 | 2/2005 | Rapoport et al. | |
| 2006/0068036 | A1 | 3/2006 | Wu | |
| 2006/0084877 | A1 | 4/2006 | Ujhazy | |
| 2006/0096596 | A1 | 5/2006 | Occhialini | |
| 2006/0249149 | A1 | 11/2006 | Meier et al. | |
| 2007/0193579 | A1 | 8/2007 | Duquette | |
| 2007/0208269 | A1 | 9/2007 | Mumford et al. | |
| 2008/0078388 | A1 | 4/2008 | Vandine | |
| 2008/0202528 | A1 | 8/2008 | Carter | |
| 2009/0038616 | A1 | 2/2009 | Mulcahy et al. | |
| 2009/0205662 | A1 * | 8/2009 | Kwok | A61M 16/0066 128/204.23 |
| 2010/0186741 | A1 | 7/2010 | Aylsworth | |
| 2010/0269824 | A1 | 10/2010 | Friberg et al. | |
| 2011/0313689 | A1 | 12/2011 | Holley et al. | |
| 2013/0116942 | A1 | 5/2013 | Hill et al. | |
| 2013/0118500 | A1 | 5/2013 | Stevens | |
| 2013/0319415 | A1 | 12/2013 | Mulcahy et al. | |
| 2014/0014110 | A1 | 1/2014 | Adams | |
| 2014/0066749 | A1 | 3/2014 | Dickerson | |
| 2014/0100470 | A1 | 4/2014 | Perry | |
| 2014/0299132 | A1 | 10/2014 | Librett et al. | |
| 2014/0373846 | A1 | 12/2014 | Kao et al. | |
| 2015/0088022 | A1 | 3/2015 | Cribbs et al. | |
| 2015/0133809 | A1 | 5/2015 | Paul et al. | |
| 2015/0320954 | A1 | 11/2015 | Suzuki et al. | |
| 2016/0144148 | A1 | 5/2016 | Crone et al. | |
| 2016/0166859 | A1 | 6/2016 | Rachapudi et al. | |
| 2016/0184538 | A1 | 6/2016 | Grashow | |
| 2016/0193437 | A1 | 7/2016 | Bao et al. | |
| 2016/0256642 | A1 | 9/2016 | Soysa et al. | |
| 2017/0079580 | A1 | 3/2017 | Moore et al. | |
| 2018/0182473 | A1 | 6/2018 | Schwaibold | |
| 2020/0121873 | A1 | 4/2020 | Hudson | |
| 2022/0184328 | A1 | 6/2022 | Hudson et al. | |

FOREIGN PATENT DOCUMENTS

| | | | |
|---|---|---|---|
| EP | 3 167 388 | 5/2017 | |
| NL | 1 039 894 | 5/2014 | |
| WO | 93/09834 | 5/1993 | |
| WO | WO-9309834 A1 * | 5/1993 | A61M 16/026 |
| WO | 2001/05460 | 1/2001 | |
| WO | 2001/97893 | 12/2001 | |
| WO | 2003/057025 | 7/2003 | |
| WO | 2010/091462 | 8/2010 | |
| WO | 2011/073814 | 6/2011 | |
| WO | 2015/022595 | 2/2015 | |
| WO | 2015/196255 | 12/2015 | |
| WO | WO2016/005186 | 1/2016 | |
| WO | 2017/055195 | 4/2017 | |
| WO | 2020/084514 A1 | 4/2020 | |

OTHER PUBLICATIONS

International Search Report for International Application No. PCT/IB2019/059057, six pages, mailed Jan. 24, 2020.

International Preliminary Report on Patentability for Application No. PCT/1B2019/059057, five pages mailed Sep. 21, 2020.

Bluetooth, Architecture Data Transport, eight pages, 2008, downloaded from <http://www.bluetooth.com/Bluetooth/Technology/Works/Data_Transport_Architecture.htm>.

Zozula et al. "Compliance with continuous positive airway pressure therapy: assessing and improving treatment outcomes" Current Opinion in Pulmonary Medicine 7:391-398 (2001).

Stepnowsky et al. "Pilot Randomized Trial of the Effect of Wireless Telemonitoring on Compliance and Treatment Efficacy in Obstructive Sleep Apnea" J. Med Internet Res. April-June; 9(2): e14, Published online May 17, 2007.

Office Action for U.S. Appl. No. 16/585,396, mailed Oct. 12, 2022, 37 pages.

Extended European Search Report for Application No. EP19876826.9, 10 pages, dated Jul. 6, 2022.

(56) References Cited

OTHER PUBLICATIONS

Examination Report No. 1 for Application No. AU 2019368820, three pages, dated Aug. 22, 2024.
Notice Requesting Submission of Opinion for Korean Application 10-2021-7015328, 13 pages, dated Aug. 13, 2024.
Notification of the First Office Action for Chinese Application No. 2019800764482, 16 pages, dated Feb. 21, 2024.

* cited by examiner

SYSTEMS AND METHODS FOR SETUP OF CPAP SYSTEMS

CROSS-REFERENCE TO RELATED APPLICATIONS

This application is a continuation of U.S. patent application Ser. No. 17/653,367, filed Mar. 3, 2022, now allowed; which is a continuation of U.S. patent application Ser. No. 16/661,250, filed Oct. 23, 2019, now U.S. Pat. No. 11,298, 480, issued Apr. 12, 2022; which claims priority to U.S. Provisional Application No. 62/749,430, filed Oct. 23, 2018, the entire contents of which are hereby incorporated by reference.

TECHNICAL OVERVIEW

The technology described herein relates techniques for assisting or guiding patients in setting up medical devices. More particularly, the technology described herein relates to techniques for setting up and using medical devices, such as CPAP and other ventilation systems, that are used in a home environment.

INTRODUCTION

Medical devices can be complex instruments that require specialized knowledge (e.g., from a doctor or other medical professional) to set up and use. However, medical professionals may not always be available to assist patients in setting up or otherwise using such medical devices. This may especially be the case where a medical device is being used in a person's home.

The complex nature of medical devices can make it difficult for patients to setup and use such devices without appropriate assistance. For example, only about a quarter of new users of certain medical devices may be able to properly set up such devices for use. This can be frustrating for patients and medical professionals. Indeed, it may even cause patients to not use medical devices—even when such devices may provide valuable treatment.

Accordingly, it will be appreciated that new and improved techniques, systems, and processes are continually sought after.

SUMMARY

In certain examples, a computer system (e.g., a mobile device such as a smart phone) is provided that wirelessly communicates with a therapy device (e.g., a device that provides CPAP therapy) that provides therapy for a patient. The computer system may be programmed to provide a series of linked instruction displays that guide a user through setting up and/or using one or more components (e.g., a flow generator, a patient interface, etc. . . . ) that are used to provide CPAP therapy.

The computer system may include programmed functionality that is used to control how CPAP-related therapy may be provided to a patient. This functionality may act as a test drive of sorts that allows a user to experience CPAP therapy through guided instructions and illustrations that are presented to the user on, for example, their own mobile phone. The programmed functionality may include a series of display screens that provide informational notices to a patient. Explanations of CPAP and control of the positive air pressure may also be provided. In certain examples, the display screens, and associated programmed functionality, may show the air pressure being increased in a stepwise manner. The increase may require the user to expressly control when pressure is increased (e.g., the pressure only increases in response to the user pressing an increase pressure button) and/or have the user expressly control when pressure stops increasing (e.g., the pressure will automatically increase unless the user presses a "stop" button).

In certain examples, the programmed functionality provided by the computer system may include detecting (e.g., during the above discussed test drive) the presence of a leak while positive air pressure is being provided to a user. Detection may be based on one or more sensors. Detection may be continuous or may be determined at each provided pressure level. In certain examples, once a leak is detected, the programmed functionality may trigger a leak remediation process. The leak remediation process may be presented to the user through a series of display screens used to assist a patient in diagnosing and addressing the leak. For example, one display screen may instruct the user to reposition the patient interface (e.g., mask), another may instruct the user to feel if any air is leaking between the mask and the face of the patient, another may instruct the patient to adjust straps of the interface, and another may instruct the user to check different parts of an airflow path (e.g., flow generator, conduit, patient interface connection, etc. . . . ). The display screens may be constructed to have the user try one solution before checking another solution. Each time the user attempts to address the leak, the system may retest to see if the leak has been fixed.

In certain examples, the display screens and associated programming may allow patients to setup a CPAP device without the assistance of an on-site medical professional. In certain examples, the display screens and associated programming may assist patients in properly fitting a patient interface to the face of the patient (e.g., so the patient interface does not leak, is comfortable, will not come off during sleep, etc. . . . ). In certain examples, the display screens may provide instructions that allow users to feel confident in using the medical equipment that is providing therapy. In certain examples, the display screens may be structured to assist patients in handling or addressing feelings of claustrophobia, anxiety, and/or fear. For example, the display screens may be used to prepare patients for experiences that may be associated with wearing a patient interface that is being supplied with positive air pressure (which can make breathing more difficult).

An aspect of certain forms of the present technology is to provide methods, computer-readable mediums, systems and/or apparatuses that improve the compliance of patients with respiratory therapy.

One form of the present technology comprises techniques for testing for leaks while positive air pressure is supplied to a patient and, if a leak is detected, providing at least one of a plurality of different troubleshooting options to the patient to address the detected leak.

One form of the present technology comprises determining, based on an identifying feature, a patient interface type for a given patient interface and storing that information. One form of the present technology comprises determining, based on an identifying feature, a flow generator type for a given flow generator and storing that information.

Another aspect of the present technology comprises selecting a troubleshooting option to display based on an identified type of flow generator, patient interface or other component. Another aspect of the present technology comprises selecting a troubleshooting option based on data related to the patient, for example physical characteristics of the patient or their prescription information.

Another aspect of the present technology comprises presenting additional or different troubleshooting options when a leak is still detected after a prior troubleshooting option has been presented.

One form of the present technology includes having troubleshooting options that include repositioning the patient interface, checking straps of the patient interface, checking if the mouth of the patient is closed, checking connectors of the CPAP system, and taking off and putting the patient interface back on.

One form of the present technology comprises setting the flow generator to a first pressure level and in response to reception of user input, causing, via wireless communication, the flow generator to increase the supply of breathable gas to a second pressure level.

Another aspect of the present technology comprises in response to determination that a leak is present based on sensor data obtained during the increase of the supply of breathable gas from a first pressure level to a second pressure level, causing, via wireless communication, the flow generator to hold at a pressure level at which the leak was detected.

In one form of the present technology, a system comprises a patient interface, a flow generator, a transceiver, a computing device that communicates with the flow generator and/or patient interface via the transceiver, and a sensor that is used to detect a physical quantity that is based on delivery of positive air pressure breathable gas to a patient.

In one form of the present technology, the computing device that is used to communicate with the CPAP system and components thereof may be formed out of multiple computing devices. One computing device may be a mobile device or personal computer in the home a patient and other may be a remotely located computer system (e.g., a cloud-based computer system) that communicates with the in-home patient computing device. In an aspect of the present technology, the determination of a leak in the delivery of air flow to the patient may be made on the remotely located computer system. In an aspect of the present technology, the determination of a leak is automatically performed. In an aspect of the present technology, a leak determination is made in response to a user input provided to the in-home patient computing device to request that a leak be checked for.

In one form of the present technology, the pressure level at which the breathable gas is supplied to the patient is increased in response to a determination that no leak is present. In an aspect of the present technology, the increase is automatically performed. In another aspect, the increase is performed in response to user provided input.

In one form of the present technology, wireless communication between an in-home computing device and the CPAP system (and/or components thereof) is accomplished via Bluetooth.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring, and/or treatment of respiratory conditions, including, devices that provide monitoring and/or treatment of, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

This Summary is provided to introduce a selection of concepts that are further described below in the Detailed Description. This Summary is intended neither to identify key features or essential features of the claimed subject matter, nor to be used to limit the scope of the claimed subject matter; rather, this Summary is intended to provide an overview of the subject matter described in this document. Accordingly, it will be appreciated that the above-described features are merely examples, and that other features, aspects, and advantages of the subject matter described herein will become apparent from the following Detailed Description, Figures, and Claims.

BRIEF DESCRIPTION OF THE DRAWINGS

These and other features and advantages will be better and more completely understood by referring to the following detailed description of example non-limiting illustrative embodiments in conjunction with the drawings of which.

DETAILED DESCRIPTION

In the following description, for purposes of explanation and non-limitation, specific details are set forth, such as particular nodes, functional entities, techniques, protocols, etc. in order to provide an understanding of the described technology. It will be apparent to one skilled in the art that other embodiments may be practiced apart from the specific details described below. In other instances, detailed descriptions of well-known methods, devices, techniques, etc. are omitted so as not to obscure the description with unnecessary detail.

Sections are used in this Detailed Description solely in order to orient the reader as to the general subject matter of each section; as will be seen below, the description of many features spans multiple sections, and headings should not be read as affecting the meaning of the description included in any section.

In certain examples, techniques and systems for facilitating the setup, acclimatization, and/or use of a medical system that may be, for example, used in a home setting are provided. In certain examples, a guided setup process may be provided through a computer system such as a mobile device (e.g., a smart phone) of the patient. The guided process may provide instructions to patients for the setup of components of a medical system. An example of a medical system includes a respiratory therapy system that may include a patient interface component (e.g., a mask), an air conduit, a flow generator (e.g., a Respiratory Pressure Therapy Device (RPT device)), a humidifier, etc. The guided process may instruct a user on setting up each component of the system for proper use. The guided process may assist in acclimatizing the user to the therapy provided by the medical device. The guided process may assist in addressing issues (e.g., a leak) that arise during use of the medical device. In certain examples, the computer system may be programmed to assist a patient in tracking progress for therapy of the patient over a period of time (e.g., hours, days, weeks, months, etc. . . . ). In certain examples, the guided setup process may act to increase the confidence that a patient has in setting up and/or operating the medical device(s) (e.g., a CPAP system or other respiratory therapy system) so as to receive the correct therapy for the patient.

Figure 1A:
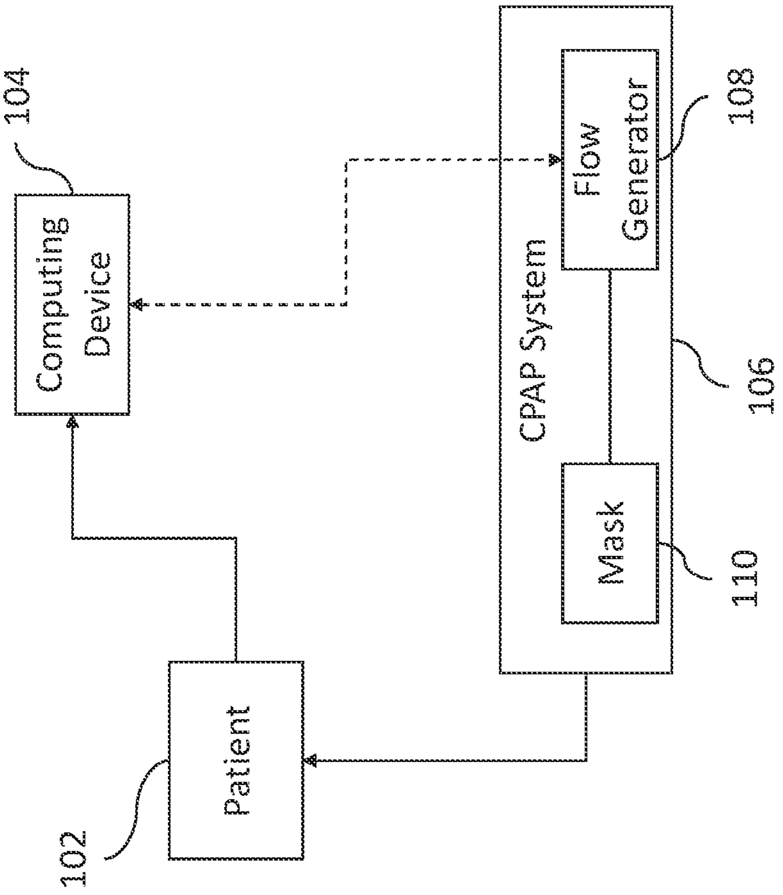
FIG. 1A is a system diagram that includes CPAP system according to certain examples.
Figure 1B:
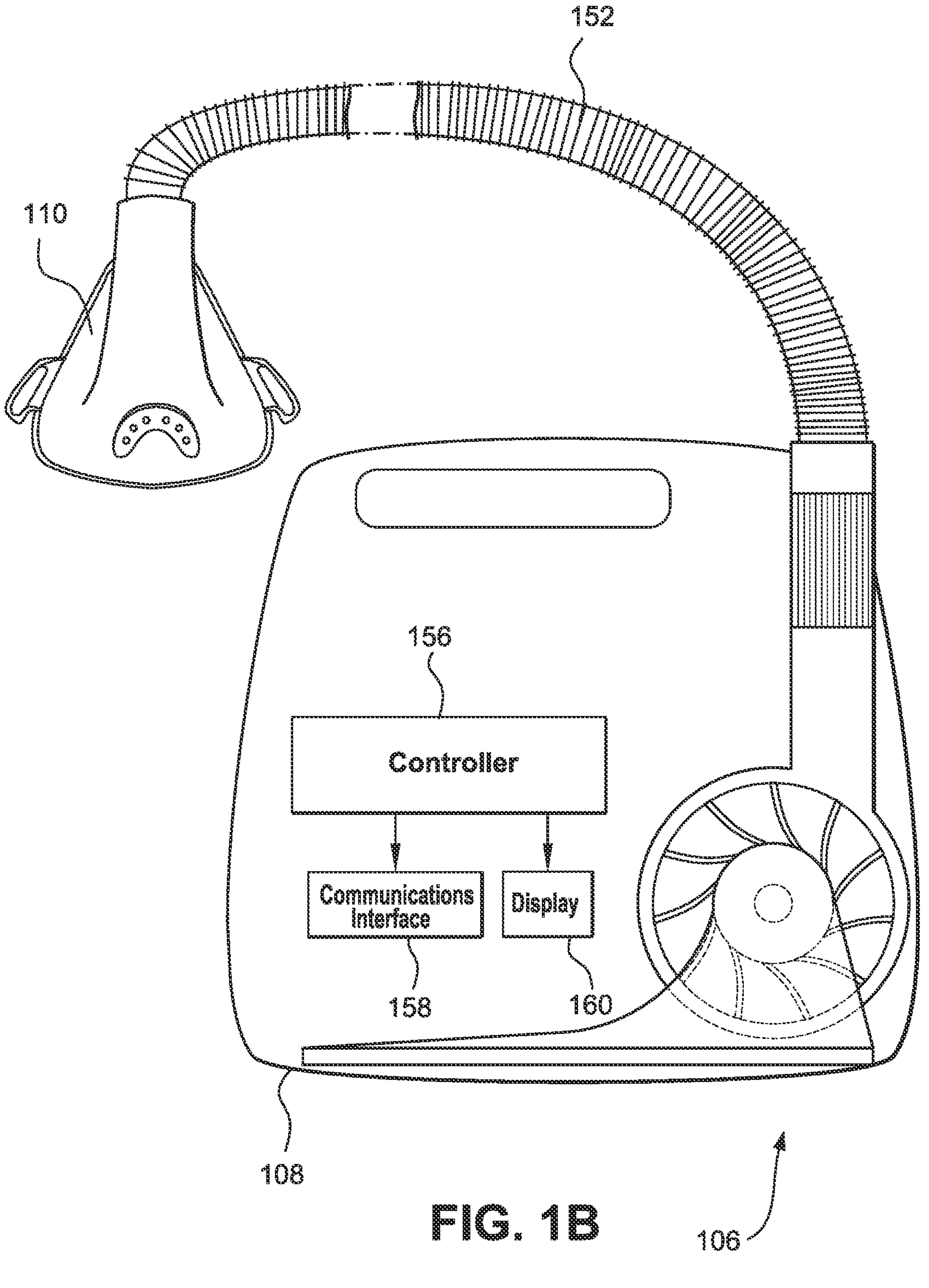
FIG. 1B shows an example CPAP system according to certain examples.

FIG. 1A is a diagram of a system that includes a CPAP system configured to communicate with a computer system, such as described in connection with FIG. 6. FIG. 1B shows the example CPAP system from FIG. 1A. FIGS. 2A-4B show display screens that may be generated and displayed on the computer system of FIG. 1A. FIGS. 5A-5E are signal diagrams of the components shown in FIG. 1A.

In many places in this document, software modules and actions performed by software modules are described. This is done for ease of description; it should be understood that, whenever it is described in this document that a software module performs any action, the action is in actuality performed by underlying hardware elements (such as a processor and a memory device) according to the instructions that comprise the software module. Further details regarding this are provided below in, among other places, the description of FIG. 6.

Description of FIGS. 1A and 1B

FIG. 1A is a system diagram that includes a CPAP system according to certain examples. FIG. 1B shows an example of the CPAP system of FIG. 1A.

FIG. 1A includes a computing device 104 that is usable by a patient 102 to which therapy is being provided via CPAP system 106. CPAP system 106 is configured to communicate with computing device 104. CPAP system 106 includes CPAP components that may be, for example, a patient interface or mask 110, a humidifier (not shown), and air conduit 152, and a flow generator 108 (which may also be called a Respiratory Pressure Therapy Device or RPT device).

It will be appreciated that while CPAP systems and CPAP therapies are discussed herein, that other types of respiratory therapy systems and therapies may also be used in connection with the example techniques discussed herein. For example, other therapies may include Non-invasive ventilation (NIV), Invasive ventilation (IV), and High Flow Therapy (HFT) therapy that may be used to treat one or more respiratory disorders.

Reparatory therapy systems may include ventilators that control the timing and pressure of breaths pumped into the patient and monitor the breaths taken by the patient. The methods of control and monitoring patients may include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

Accordingly, whenever it is described herein that a CPAP system may operate as described, such description may also apply to other types of respiratory therapy systems. The techniques herein may be applied to different types of respiratory therapy systems and ventilators that are used to provide different types respiratory therapies for treating various respiratory disorders.

Figure 6:
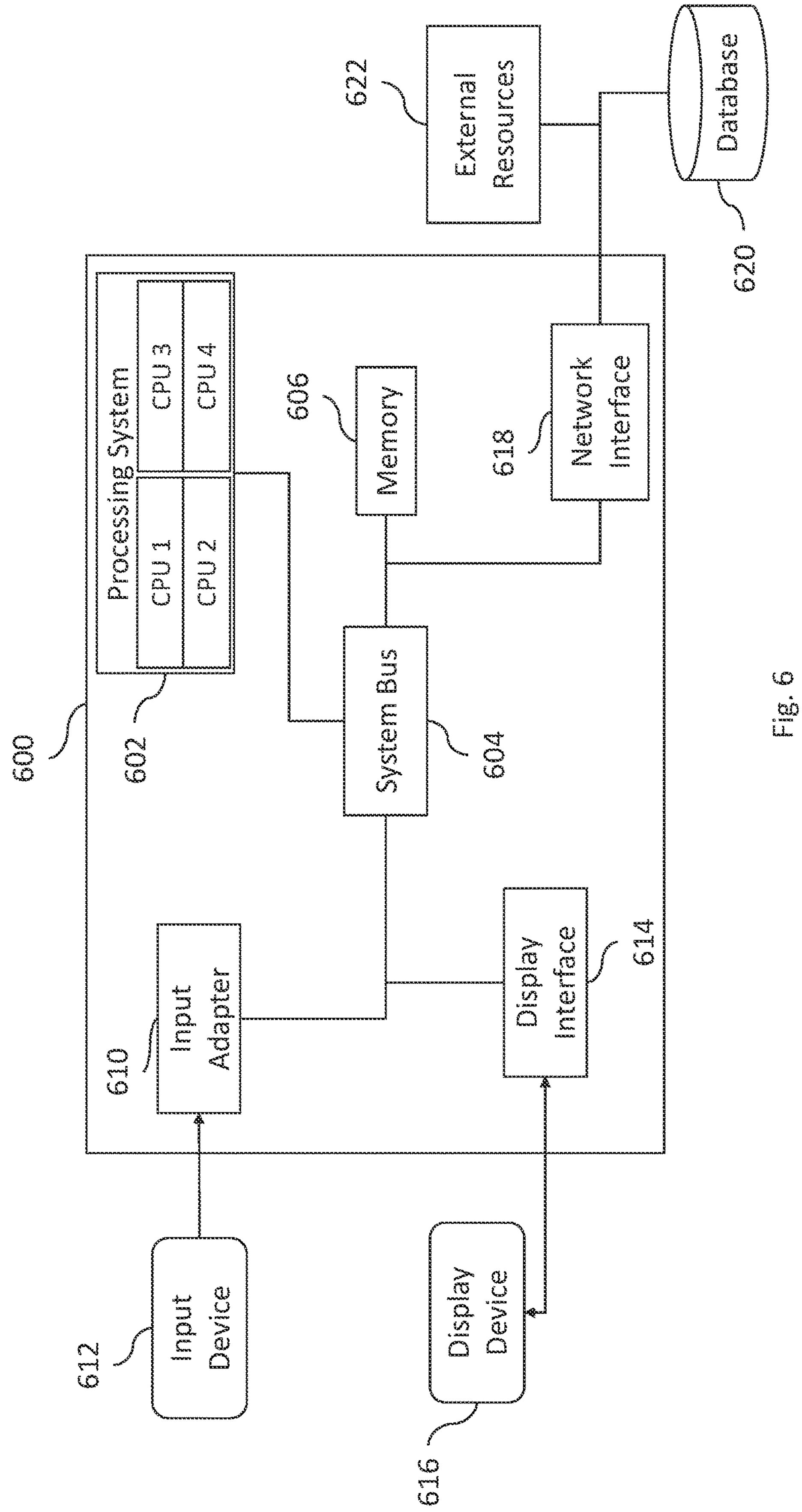
FIG. 6 shows an example computing device that may be used in some embodiments to implement features described herein.

Returning to FIG. 1, computing device 104, of which an example is shown in FIG. 6, may be a mobile device (e.g., a smart phone), desktop computer, laptop computer, tablet, or the like. In certain examples, the computing device 104 and the CPAP system 106 are separate devices that communicate with one another via a wireless data communications protocol. For example, the computing device 104 may be a mobile phone or tablet that includes programmed functionality (e.g., a software module, application, or "app") that causes the computing device 104 to carry out functionality described herein. In certain examples, some or all of the functionality that computing device 104 provides (e.g., as discussed herein) is incorporated into CPAP system 106. For example, functionality related to detection of a leak may be carried out by CPAP system 106 (or any of the components thereof). In certain examples, all of the functionality of the computing device may be incorporated into or provided by the flow generator 108 or other component of the CPAP system 106.

Computing device 104 may communicate with CPAP system 106 via wired (e.g., via a serial port, or other type of data communication port and protocol, Ethernet) or wireless communications (e.g., via Bluetooth™, 802.11x, NFC, etc.). In certain examples, as discussed in greater detail below, a user may configure CPAP system 106 to communicate with computing device 104 by, for example, pairing the computing device with the CPAP system using Bluetooth or other wireless communication protocol.

Computing device 104 and/or CPAP system 106 (or components thereof) may be configured to communicate (e.g., via a network interface 618) with external computer systems (e.g., external resources 622) via a data communications network (e.g., the Internet 110 or the like). External computer systems may include, for example, cloud-based computer systems (e.g., Amazon AWS, Microsoft Azure, etc. . . . ) or other computer systems that may store (e.g., in a database or the like), for example, data on setup for CPAP systems and components thereof.

In certain examples, CPAP system 106 may use the communication functionality of computing device 104 for communicating to external computing resources. For example, CPAP system 106 may communicate data to computing device 104 via Bluetooth (or other wireless or wired protocol) and computing device 104 may then relay or route such data communications to external computing resources.

In certain examples, computing device 104 may include or be a plurality of computing devices. For example, a first computing device may be a mobile device and a second computing device may be a desktop computer or the like. In certain examples, multiple computing devices may be programmed to communicate with a single CPAP system 106. For example, a patient may use their tablet computer (a first computing device) at one instance and their smart phone (a second computing device) in another instance. In certain examples, one computing device (e.g., a person's mobile phone) may be programmed to communicate with multiple different CPAP systems. For example, a couple may each have a CPAP system that they use for treatment and one tablet computer shared by the couple may be used to control and/or communicate with both of the respective CPAP systems that are separately used by each person.

FIG. 1B shows an example of CPAP system 106 according to certain examples. CPAP system 106 includes patient interface 110, conduit 152 (which may also be called an air circuit), and flow generator 108 (e.g., a respiratory pressure therapy (RPT) device). In certain examples, a humidifier may be included. Example details of these components are discussed in greater detail below. Depending on the nature of the CPAP system other types of CPAP components may also be included.

Patient interface 110 may include one or more of the following functional aspects: a seal-forming structure, a plenum chamber, a positioning and stabilizing structure, a vent, one form of a connection port for connection to conduit 152, and/or a forehead support. In certain examples, the functional aspect may be provided by one or more physical components. In some forms, one physical component may provide one or more functional aspects.

In certain examples, the seal-forming structure is arranged to surround an entrance to at least one airway of the patient so as to facilitate the supply of air at positive pressure to the at least one airway.

In certain examples, a patient interface that is unable to comfortably deliver a level of positive pressure to a patient's airways that is more than a threshold level may be unsuitable for respiratory pressure therapy. In certain examples, patient interface 110 may provide a supply of air at a positive pressure of at least 6 cmH2O, of at least 10 cmH2O, or of at least 20 cmH2O with respect to ambient air pressure.

In certain examples, a seal-forming structure of the patient interface provides a target seal-forming region, and may additionally provide a cushioning function. The target seal-forming region is a region on the seal-forming structure where sealing may occur. It will be appreciated that the region where sealing occurs may change within a given treatment session, from day to day, and from patient to patient, depending on a range of factors including, for example, where the patient interface was placed on the face, tension in the positioning and stabilizing structure and the shape of a patient's face.

In certain examples, the target seal-forming region is located on an outside surface of the seal-forming structure. In certain examples, the seal-forming structure is constructed from a biocompatible material (e.g., silicone rubber).

In certain examples, the seal-forming structure forms a seal on: 1) on a nose bridge region or on a nose-ridge region of the patient's face, 2) an upper lip region (e.g., the lip superior) of the patient's face, 3) a chin-region of the patient's face, and/or 4) a forehead region of the patient's face (e.g., where the plenum chamber may cover the eyes of the patient when the patient interface is worn by the patient). In certain examples, the seal-forming structure forms may comprise a pair of nasal puffs, or nasal pillows, each nasal puff or nasal pillow being constructed and arranged to form a seal with a respective naris of the nose of a patient In certain examples, the plenum chamber has a perimeter that is shaped to be complementary to the surface contour of the face of an average person in the region where a seal will be formed. When used by a patient, a marginal edge of the plenum chamber is positioned in close proximity to an adjacent surface of the face. Actual contact with the face may be provided by the seal-forming structure discussed herein. In certain examples, the seal-forming structure may extend about the entire perimeter of the plenum chamber. In certain examples, the plenum chamber and the seal-forming structure are formed from a single homogeneous piece of material.

In certain examples, the patient interface 110 may include positioning and stabilizing structures used to hold the patient interface in a sealing position on the face of the patient. In certain examples, the included positioning and stabilizing structure may include straps, ties, or other component that acts to secure the mask to the head of a patient.

In certain examples, the patient interface 110 may include a vent that is constructed to allow for the washout of exhaled gases (e.g., carbon dioxide) from the patient as a result of breathing. In certain examples, such a vent is configured to allow a continuous vent flow from an interior of the plenum chamber to ambient while the pressure within the plenum chamber is positive with respect to ambient. The vent may be configured such that the vent flow rate has a magnitude sufficient to reduce rebreathing of exhaled CO2 by the patient while maintaining the therapeutic pressure in the plenum chamber while a patient interface is being used by the patient. In certain examples, the vent includes a plurality of holes, for example, about 20 to about 80 holes, or about 40 to about 60 holes, or about 45 to about 55 holes.

In certain examples, the patient interface 110 may include a connection port that allows for a structural coupling of the conduit 152 to patient interface to thereby deliver above atmospheric gas to the patient from the conduit 152.

In certain examples, the patient interface 110 includes a forehead support structural support that allows the patient interface to engage with the forehead of the patient.

In certain examples, conduit 152 is constructed to allow a flow of air between the flow generator 108 and the patient interface 110. In certain examples, conduit 152 includes one or more heating elements (e.g., a heated wire circuit) configured to heat the air in the air conduit 152. The heating element may be controlled by controller 156 of the flow generator 108.

Flow generator 108 includes controller 156, a communication interface 158, and one or more displays 160. Flow generator 108 may include an outlet that is configured to couple to conduit 152. Flow generator may also include a blower that is configured to supply gas (e.g., breathable air) at pressure between about 2-40 cmH2O, or in the range of 4-20 cmH2O to patient interface 110 via an air delivery conduit 152. A flow sensor and/or a pressure sensor may be included at the outlet of the flow generator 108 and/or may be included with the patient interface 110 or conduit 152.

Controller 156 may be a hardware processor or processing system (e.g., such as described in connection with FIG. 6). Communication interface 158 may be a communication or network interface such as that described in FIG. 6 (e.g., network interface 618). Display 160 may be a display such as that described in FIG. 6 (e.g., display device 616). In certain examples, display 160 includes a light or other visual indicator.

In certain examples, flow generator 108 may include multiple communication interfaces 158. For example, one communication interface may be configured for shorter range wireless communication (e.g., Bluetooth, RFID, NFC, etc. . . . ). Another communication interface may be a wired communication interface that is configured to communicate via, for example, a wired communications protocol (e.g., Ethernet or TCP/IP). In certain example embodiments, communication interface 158 may include a cellular communications module that is configured to communicate using cellular wireless communications. Another communications interface may be included that communicates with other components (e.g., sensors, patient interface 110, conduit 152, etc. . . . ) of CPAP system 104. For example, sensors included with the patient interface 110 and/or conduit 152 may communicate sensed data, such as pressure or flow data, to communications interface 158. In certain examples, communications interface 158 may include or implement a wired or wireless protocol to enable communication with computing device 106 and/or other computing resources.

In certain examples, patient interface 110, conduit 152, flow generator 108, and/or other CPAP component types (e.g., a humidifier, etc. . . . ) may include one or more identifying features that may be used to uniquely distinguish the type of component (e.g., a nasal mask versus a full mask mask) and/or a specific component being used by a patient (e.g., each component may have a unique identifier—e.g., a GUID) that is used to distinguish a particular component from other components (even if they are the same type of component). In certain examples, one identifying feature may be used to identify the type of CPAP component and another may be used to specifically identify a particular CPAP component. In certain examples, the identifying feature is implemented via a bar code, RFID (e.g., active or passive), a resister, or the like.

In certain examples, a given CPAP component may also include a memory device for storing data related to that CPAP component. The data may be for a specific patient (e.g., that is to use the component). In certain examples, the data may be accessed via wireless or wired data communications (e.g., via RFID). In certain examples, data from sensors for a given component may be written directly to a memory device of the CPAP component carrying the sensor. For example, patient interface 110 may include a sensor for measuring pressure and a memory device (e.g., flash memory) disposed with the mask to storing pressure data recorded by the pressure sensor.

Figure 2A:
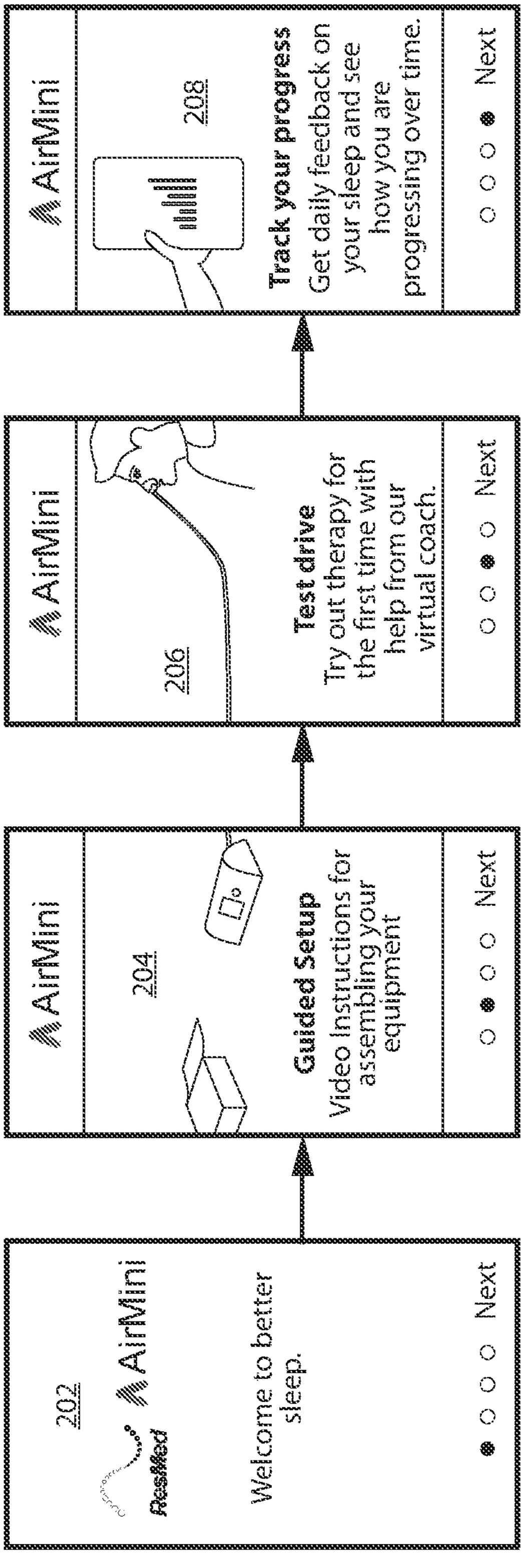
FIGS. 2A-2C shows a series of screens that assist a user in setting up a CPAP device according to certain examples.
Figure 2B:
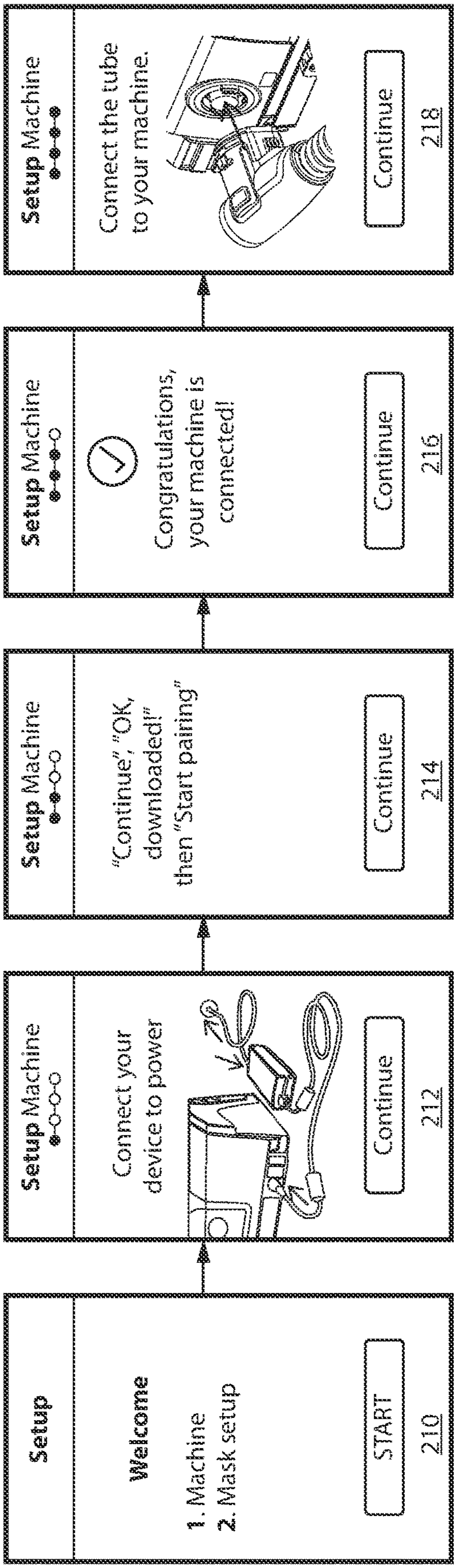
Figure 2C:
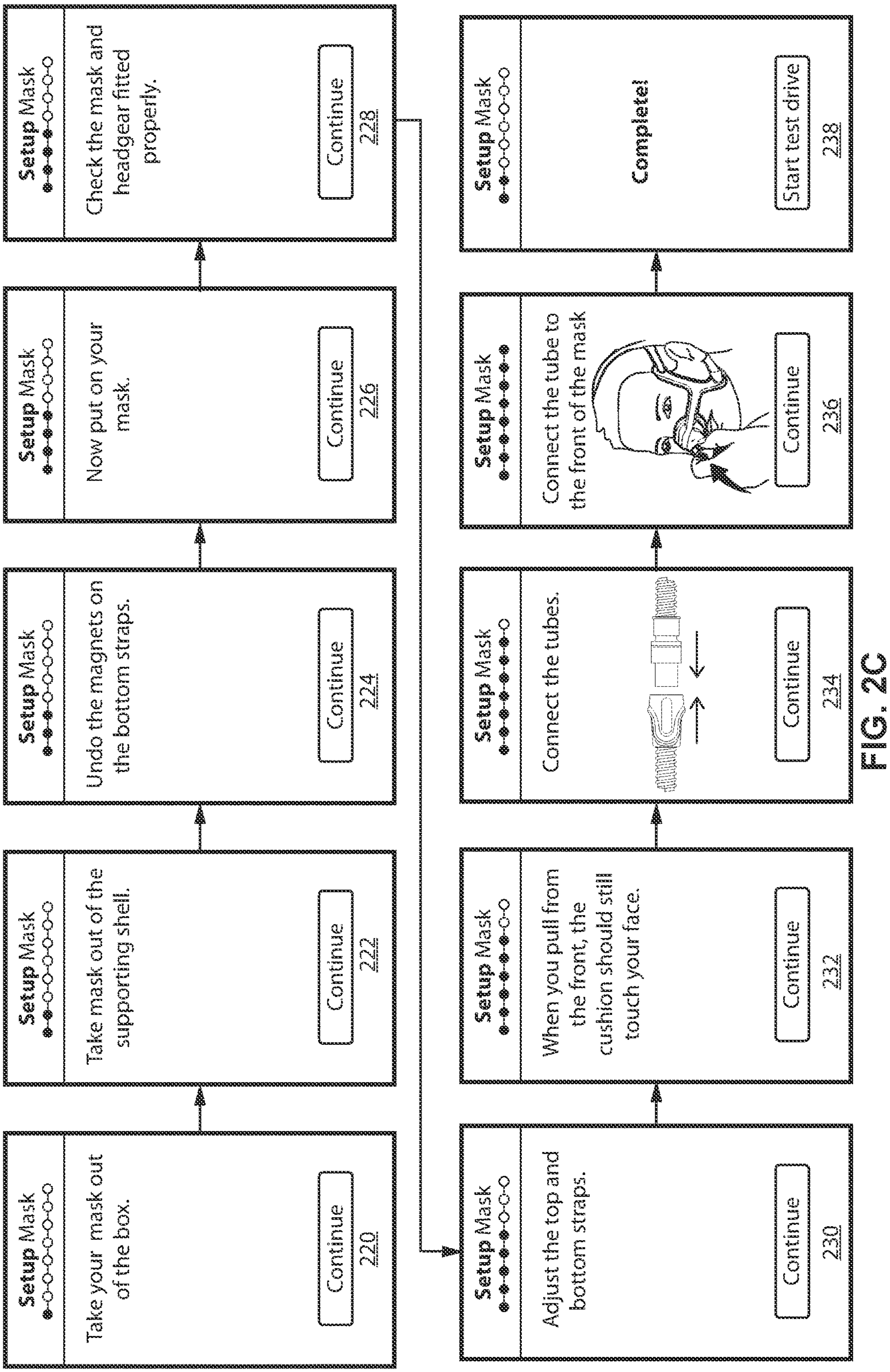

Description of FIGS. 2A-2C

FIGS. 2A-2C shows a series of screens that assist a user in setting up a CPAP device according to certain examples.

In general, FIGS. 2A-4 show display screens that may be generated by a computing device (e.g., computing device 104) and displayed on a display device (e.g., 612) that is coupled to the computing device. The display screens may be generated as part of a computer program, application program, or “app” that is executed by the computing device 104 to thereby create and display the display screens. In certain examples, the display device is integrated into the physical structure of the computing device (e.g., when the computing device is a smartphone). In certain examples, the display device is separate from the computing device (e.g., a monitor used with a desktop computer).

In certain examples, a patient may be prompted to download (e.g., from a web site or “app” store) and/or install (e.g., from a CD or a flash drive) a specific application program to a computing device of the patient. The application program may be installed onto, for example, a smart-phone of the patient. In the examples discussed in connection with FIGS. 2A-4, the shown display screens may be generated by the same application program. However, it will be appreciated that in other examples different display screens may be generated and displayed according to the execution of different application programs. For example, the display screens in FIGS. 2A-2C may be generated with one application program and the display screens in FIG. 4 may be generated by a separate application program.

The display screens may assist in helping a patient set up their CPAP (or other medical) system in, for example, their own home. The display screens may provide reassurance to a patient who is trying respiratory pressure therapy (e.g., CPAP therapy) for the first time. The display screens and associated programming may be used to provide an interactive process that allows a user to control aspects of the setup and acclimatization process. The programming and display screens may provide feedback (e.g., in real-time with provision of therapy) to the patient. The programming and display screens may provide advice and/or instructions to assist patients in addressing (or avoiding) one or more potential problems with their therapy.

FIG. 2A shows example display screens that may be displayed to a patient via a display associated with computing device 104. Upon launching or starting an application program (or starting a process within an already started application program) with the computing device, an introduction screen 202 may be displayed to the patient. Introduction screen 202 may include an introduction video or other explanation that introduces a patient to the systems, components, and/or therapy (e.g., what is CPAP) that will be provided to the patient.

The introduction part of the application program may include an explanation of the different functionality found in the program. A first display screen 204 may relate to a guided setup aspect of the application program. This is discussed in more detail in connection with FIGS. 2B and 2C. The setup portion may be a guided setup process that includes video instructions for assisting a user in setting up a CPAP system and its associated components.

A second display screen 206 may provide an introduction for test drive functionality included in the application. This is discussed in greater detail in connection with FIGS. 3A-4 and includes a process for guiding a patient through therapy for the first time with a virtual coach. This may also include instructional tips for resolving issues that may arise during this testing of the provided therapy. A third display screen 208 may include a discussion of functionality that may be used to track and/or receive feedback on therapy.

Turning to FIG. 2B, display screens that are included as part of a setup process are shown. Display screen 210 may be provided to indicate to the patient the different aspects of setup that are to be performed. Specifically, setup for a CPAP system may include at least setting up a machine (e.g., flow generator 108) and configuring and setting up a patient interface (e.g., mask that a patient will be using during the therapy). Other setup sub-processes may also be indicated (e.g., for setting up a humidifier). In certain examples, the type of setup process and what is included in the setup process may be dynamically determined based on the type of CPAP system that the patient is using. For example, if the patient’s CPAP system includes a humidifier then a humidifier portion of the setup process may be included. However, if a humidifier is not included in the patient’s CPAP system, then it may be skipped or not displayed as part of the setup process.

Part of the setting up of the CPAP system may include prompting the patient to load their prescription information into the computing device 104. In certain examples, the prescription for the patient may be used to customize the setup instructions that are provided to the patient. For example, the setup for a nasal mask that is prescribed to one patient may be different than the setup instructions provided to a second patient that is prescribed a full face mask.

In certain examples, the setup process that is performed in conjunction with the display screens may be accompanied by audio instructions that are output from a speaker of the computing device 104. In certain examples, videos or animations may be used to convey information to a patient during the setup process. In certain examples, the setup process may include instructions and/or display screens that instruct a patient on how to unpack or operate the different components of the CPAP system.

As noted above, the setup process may include a setup machine portion (e.g., for the flow generator 108) and a setup mask portion (for patient interface 110).

Both the setup machine and setup mask portions of the overall setup process may include graphical indicators that show the patient how far into the setup process the patient has proceeded. For example, in display screens 212-218, a series of dots are included in an upper portion of the various display screens that indicate how far along a patient is into the setup process for setting up the "machine" (e.g., the flow generator or RPT device). Display screen 212 is the first of four screens or steps and display screen 218 is the fourth of four.

Display screen 212 starts the setup machine process (e.g., the first step on the process as indicated by the filled in first of four dots) by instructing the patient to plug in and connect the flow generator to a power source. As noted above, the instructions may be customized based on the type of machine being used by the patient (which may be recognized based on the prescription information or other technique for recognizing the type of machine being setup—e.g., image recognition, bar code identification, RFID, etc. . . . ).

In certain examples, the application may then instruct, as illustratively shown with display screen 214, the patient on establishing a communication link between the machine and computing device 104. For example, the application may instruct the user to pair the computing device 104 with the newly plugged in machine (e.g., flow generator 108). In certain examples, other CPAP components (e.g., a humidifier, air conduit, patient interface, etc. . . . ) may also be paired (or other types of communication links established) with computing device 104.

Once a communication link is established (e.g., via Bluetooth pairing or the like), display screen 216 may be displayed to indicate to the patient that the computing device 104 is communicatively connected to the CPAP system 106 (or one or more components, such as flow generator 108 or mask 110, thereof).

Display screen 218 then illustrates how air conduit 152 may be coupled to or connected to an outlet of flow generator 108. In certain examples, the flow generator 108 and/or air conduit 152 may be able to recognize when a successful connection has been achieved. For example, the outlet to the flow generator may include an electrical connection that is used to identify when an air conduit 152 is successfully connected. In response to detecting successful connection, a message may be sent to computing device 104 and a corresponding display screen may be generated and displayed to the patient indicating that connection was successful. Conversely, if an error in the connection is detected then a message indicating as such may be sent to the computing device 104 from the CPAP system 106 and a corresponding display screen with an error message may be generated and displayed to the patient. Thus, the patient may receive active feedback on, for example, their mobile phone regarding the setup of the CPAP system and components thereof.

In certain examples, additional instructional details may be included in further display screens. Such display screens may show, for example, how to properly install a humidifier, or install a heated tube. Again, such display screens may be generated and displayed based on the specific needs of an individual patient. In other words, if a given patient does not have a humidifier or a heated tube, then such instructions may not be displayed for that patient as part of the setup process and associated display screens. As with the above instructions, these instructions may also include feedback to confirm the successful or correct installation of a given CPAP component has occurred.

FIG. 2C includes a series of display screens that assist a user in setting up a mask (a patient interface). In certain examples, the nature of the specific display screens may be generated based on the type of mask or patient interface that the patient is using. The type of patient interface may be determined from the earlier mentioned prescription information, recognition of a bar code that is carried by the mask, use of image recognition, RFID, or other techniques for identifying the type of patient interface that is being setup. In certain examples, what information is conveyed to the patient or what display screens are generated and shown may be based on the recognition. In certain examples, the order of the display screens (e.g., 220-238) and what instructional information is presented to the user may be based on the recognized information (e.g., prescription information, recognized component type, etc.).

Display screen 220 indicates that the patient should take the mask out of the box in which it is packaged. In certain examples, an image, video, or animation may be displayed to the patient to demonstrate how to remove the mask from the box or other packaging.

In certain examples, the patient interface may come in its own packaging. Accordingly, for example, display screen 222 indicates that the patient should take the mask out of a supporting shell (e.g., packaging material included in the box that may be included around the mask). In certain examples, an image, video, or animation may be displayed to the patient to demonstrate how to remove the supporting shell or other packaging material.

Display screens 224 and 226 instruct the patient on how to put on the mask. Screen 224 may be utilized, for example, with a mask that includes magnetic headgear connects. Alternative or additional screens could be used in connection with masks that use different headgear, for example, headgear with snap connects, Velcro, elastic bands, etc. Screens may visually show different elements of the mask and how such elements should be setup or arranged for use of the mask. In the included example, screen 224 instructs the patient to undo the magnets on the bottom straps of the mask to release the headgear and allow the mask to be properly positioned. In certain examples, an image, video, or animation may be displayed to the patient to demonstrate how to undo the magnets.

Display screen 226 instructs the patient to put on the mask. In certain examples, an image, video, or animation may be displayed to the patient to demonstrate how to put on the mask.

Display screen 228 instructs the patient to check that the mask and headgear are properly fitted. In certain examples, an image, video, or animation may be displayed to the patient to demonstrate how to properly fit the mask and/or headgear to the face of the patient. Such videos may allow a patient to see how a mask should be fitted to the face of a person.

Display screen 230 instructs the patient to adjust the top and bottom straps. In certain examples, an image, video, or animation may be displayed to the patient to demonstrate adjustment of the top and/or bottom straps of the mask. In certain examples, the top and bottoms straps should snugly fit to the patient face without being too tight. This display screen, and display screen 232, may facilitate correct adjustment of the straps by the patient to prevent over and/or under tightening of the straps.

Display screen 232 instructs the patient with additional information on how adjusting the top and/or bottom straps of the mask should affect the mask. In particular, display screen 232 may indicate that a cushion portion of the mask should still be in contact with the face of the patient when the mask is pulled from the front.

Another step in the setup process for the patient interface includes display screen 234 that instructs the patient to connect one or more tubes or conduits to each other and a display screen 236 that shows a patient wearing a mask with a connection to an air conduit.

In certain examples, specific instructional notes may be included depending on the nature of the component (e.g., patient interface, air conduit, etc. . . . ) being set up. For example, if a connection between a patient interface and air conduit is provided and the type of connector that is being used between the two components includes dual clips on either side of a connector, then the displayed instructions on a display screen may include a note reminding the patient to ensure both sides of the connector are securely clipped. Such pinpoint instructions may prevent future problems (e.g., leaks occurring in the connection).

At 238, the setup process for the patient interface is finished and the patient is notified.

In certain examples, finishing a setup of a component and/or a given display screen may be logged to a data file or the like. In certain examples, the data of a patient's progress in the setup of the equipment may be transmitted to a remote computing device. This may allow remote users (e.g., medical or customer support personnel) to verify that the setup for a given component has been completed. In certain examples, data from the CPAP system 104 (and/or components thereof) may be retrieved for each of the components that is set up and additionally logged. For example, the patient interface and/or air conduit may be structured to electronically determine that one has been correctly installed with the other. Data of such a determination may be transmitted to the computing device 104 for storage in association with a given setup process (e.g., FIG. 2C) and/or a specific step in that process (e.g., a step in the process that is associated with display screen 234). Such recorded data may be transmitted to remote computing systems (e.g., 622 in FIG. 6) for storage therein.

Figure 3A:
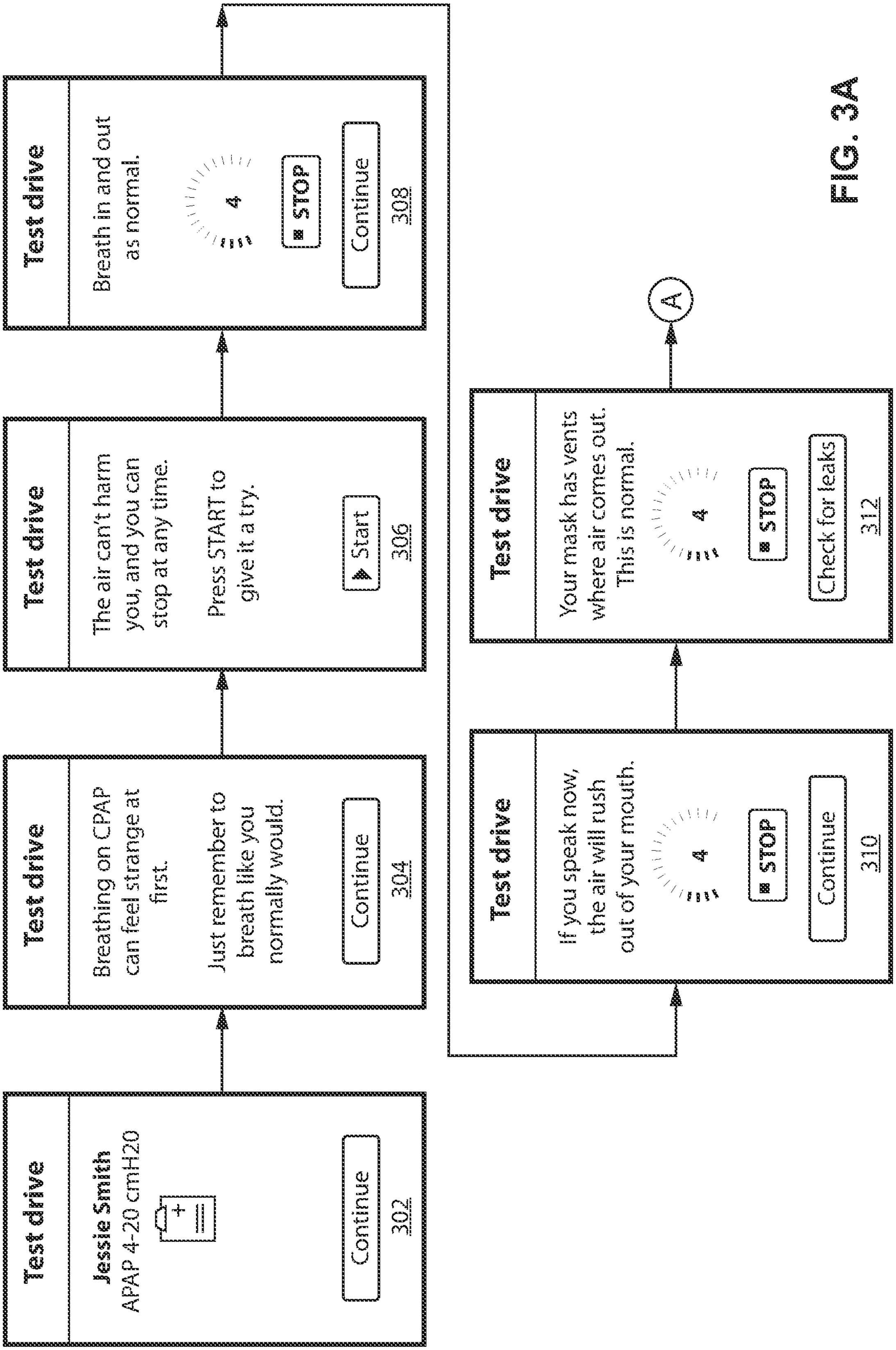
FIGS. 3A-3C show a series of screens that assist a user in starting CPAP therapy according to certain examples.
Figure 3B:
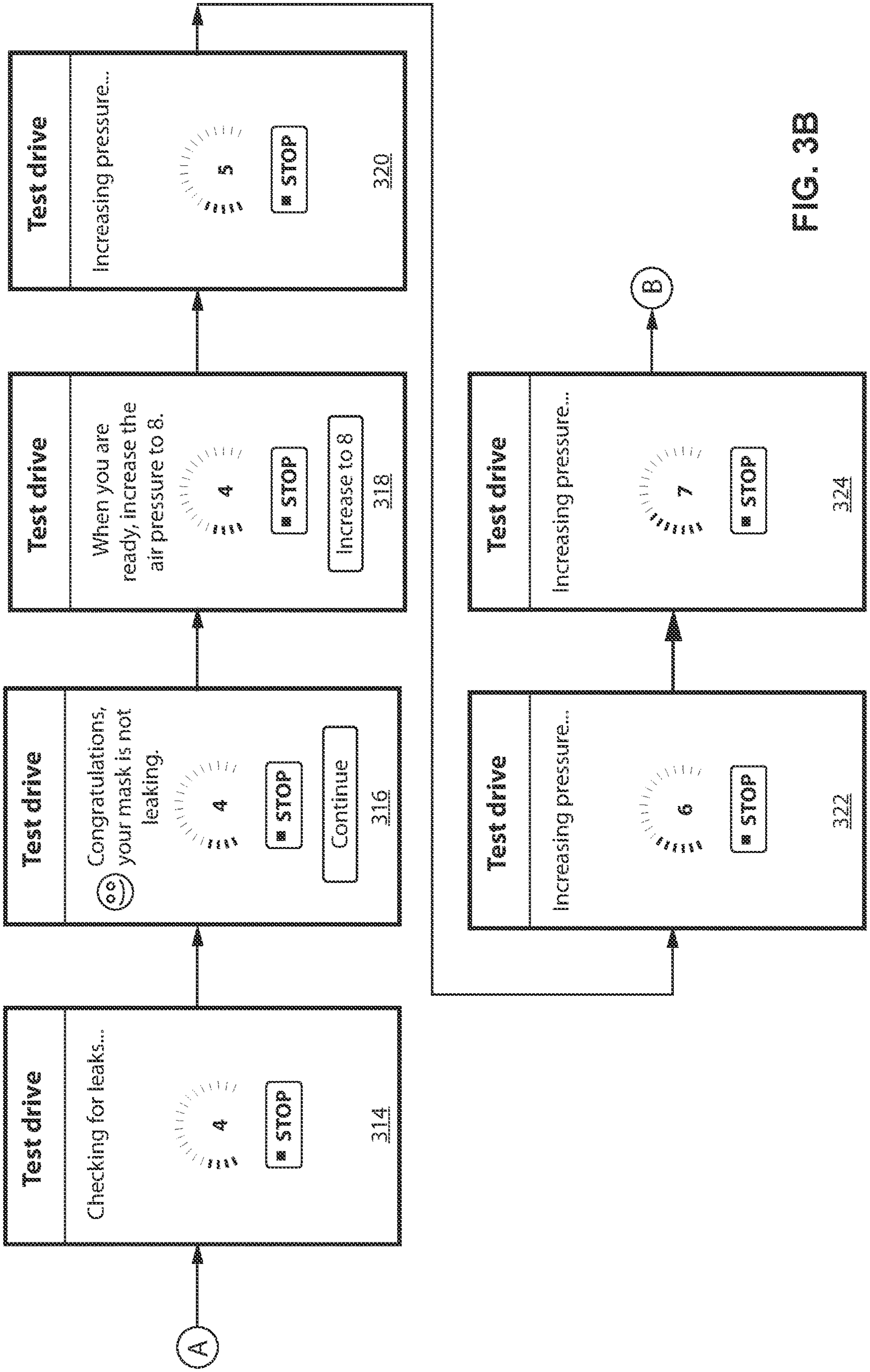
Figure 3C:
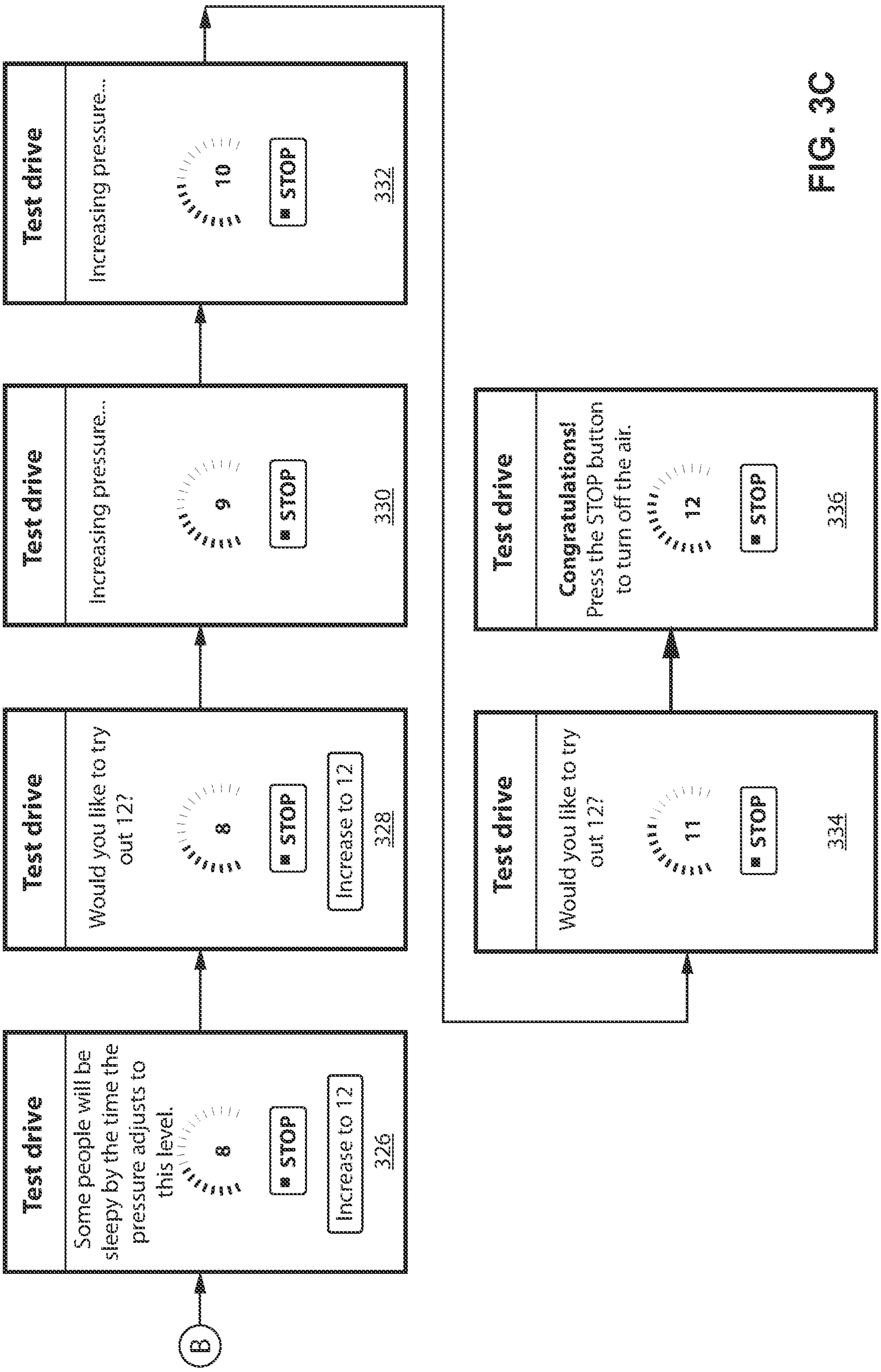

Description of FIGS. 3A-3C

FIGS. 3A-3C show a series of screens that assist a user in starting or acclimatizing to CPAP therapy according to certain examples. Once the CPAP system 106 and components thereof (e.g. the flow generator, mask, humidifier, air conduit, etc. . . . ) is set up as discussed in FIGS. 2A-2C, then the patient may elect to start a so-called test drive of the CPAP system. A test drive may function to acclimate a patient with the CPAP system including, for example, the feeling of being supplied with positive air pressure and/or correct placement of the patient's mask. In certain examples, the test drive process may start automatically. For example, upon completion of setting up the mask as shown in FIG. 2C, the application program being executed on the computing device 104 may automatically load the test drive process that is discussed in connection with FIGS. 3A-3C (and FIGS. 5A-5E). In certain other examples, the test drive process may be expressly triggered by the patient. For example, the patient may start a test drive process by manually selecting a test drive icon on the like.

Upon starting a test drive process, display screen 302 may be displayed. Concurrently with the start of the test drive process, in certain examples, the computing device 104 may perform a final "check" of all components to ensure that they are appropriately connected to one another and ready to start the test drive session (or therapy).

In certain examples, display screen 302 may include a video or other explanation that describes the therapy to be provided to the patient. For example, if the flow generator is configured to continually determine and correspondingly adjust a required therapy pressure throughout a patient's therapy session, then the functionality of flow generator and/or therapy associated therewith may be explained to the patient at this point. Other types of therapy, features, or functionality may be explained as well. For example, if a bi-level flow generator is used, then an explanation may be provided that the flow generator operates by providing different pressures during inhalation and exhalation. In certain examples, display screen 302 may include an explanation that the test drive process is different from normal use. As noted herein, the instructional materials presented to the patient may be tailored to the specific patient, the prescription for the patient, characteristics of the patient or prescription, and/or the type of CPAP system (or components thereof) being used. For example, depending on the patient's therapy, an appropriate explanation for a given patient may be presented.

In certain examples, control of the pressure being supplied by the flow generator 108 and/or other functionality of the CPAP system 106 may be passed to the computing device 104 (e.g., the computing device 104 may be used to issue commands to the CPAP system 106). This control may be facilitated through, for example, the previously set up Bluetooth wireless communication link. Such control may allow the computing device 104 to, for example, control the level of positive air pressure being supplied from the flow generator 108 to the mask 110 worn by patient 102.

Upon pressing the continue button in display screen 302, display screen 304 may be displayed. Display screen 304 includes an explanation for the patient that may help to pre-empt panic and/or fear from arising when a patient first tries therapy (e.g., due to being supplied with positive air pressure). In certain examples, a picture, video, audio, or animation may accompany or replace the textual explanation.

Upon triggering the continue button in 304, the display screen 306 may be displayed. Display screen 306 includes a start button that is triggerable by the patient and a reminder that the test drive process may be stopped at any time (e.g., by hitting any of the stop buttons included in the display screens discussed herein).

Upon triggering the start button in display screen 306, the computing device 104 starts the test drive process. Aspects of this process are discussed in greater detail in FIGS. 5A-5E, but the process may include having the computing device 104 send an instruction to the flow generator to begin supplying positive air pressure at a set level) as shown at display screen 308 (e.g., 4 cmH2O as indicated by the "4" in screen 308. It will be appreciated that while pressure is supplied to the patient, different informational messages may be displayed to the user. For example, display screen 308 reminds the patient to breathe normally and display screen 310 informs the patient that opening their mouth will cause air to rush out (e.g., due to the pressure differential). Display screen 312 also instructs the patient on the operation of the mask by notifying the patient that the vents in the mask allow air to be vented. As noted above, the patient may stop the process by pressing any of the stop buttons included in the display screens. Display screen 312 also includes a check for leaks button that allows a user to trigger functionality to check the CPAP system 106 for leaks.

In certain examples, the leak checking aspects are automatically performed in the background (e.g., no user intervention is required). In certain examples, leak checking is performed throughout the test drive process. In certain examples, leak checking is expressly triggered by the patient (e.g., by hitting the check for leaks button). In certain examples, the leak checking process is performed at specific points in the test drive process. For example, after supplying air to the patient for a period of time the computing device may collect data from the CPAP system 106 and determine if a leak is present based on the acquired data. In certain examples, a leak check is performed in correspondence with each increase in pressure. In certain examples, detection of a leak during a pressure increase may cause the flow generator (via a command from computing device 104) to pause the pressure increase. For example, if a leak is detected at 6 cmH2O (e.g., 322 in FIG. 3B), then the flow generator may automatically hold the pressure at 6 cmH2O until the leak is fixed (e.g., as discussed in connection with FIG. 4). Upon fixing the leak, then the process of increasing the pressure may resume (e.g., to 7 cmH2O).

In any event, turning to FIG. 3B, display screen 314 shows the leak check process being performed. If a leak is detected, then the process discussed in connection with FIG. 4 may be displayed and performed. If no leaks are found, then display screen 316 is shown indicating as such.

If no leaks are detected, then display screen 318 may be shown to patient. Display screen 318 includes a prompt that is presented to the patient to increase the pressure to another pressure level (e.g., 8 cmH2O). Upon the patient pressing the increase button, the computing device may communicate to the CPAP system 106 (e.g., the flow generator thereof) to increase pressure to the selected pressure level. In certain examples, the patient may manually select the next pressure level (e.g., 6 cmH2O). In certain examples the manual selection may be less than or equal to a displayed default level (e.g., 8 cmH2O as shown in the button of display screen 318).

Subsequent display screens 320, 322, and 324 show increases in the provided pressure in a stepwise manner (e.g., 5, then 6, then 7, etc. . . . ). In certain examples, each stepwise increase may be controlled by the computing device 104 sending a new instruction to the CPAP system 106 to increase the pressure. In certain examples, the CPAP system 106 may automatically stepwise increase the pressure and report to the computing device (e.g., via the wireless communication link) the current pressure. In other words, in some instances the computing device "controls" the pressure increases performed by the CPAP system. Alternatively, or in addition, the CPAP system (or flow generator thereof) "controls" the pressure increases and reports the pressure level back to the computing device for display thereon (e.g., as part of display screens 320, 322, 324, etc. . . . )

It will be appreciated that for each pressure increase (or continually throughout the process), that the above noted leak checking process may be performed. Also, a patient may stop the pressure increase by hitting the stop button that is shown in display screens 318-324. In certain examples, hitting the stop button may pause the automatic pressure increases. For example, if a patient presses the stop button at 6, then system may maintain the pressure level at 6 cmH2O. In certain examples, triggering the stop resets the pressure level to a prior pressure level (e.g., back to 4 cmH2O). In certain examples, triggering the stop button turns off the supply of positive air pressure that is being supplied to the patient from the CPAP system and flow generator. In certain examples, a button for pausing the pressure increase and a button for shutting off the provided pressure may be separately provided within the same display screen.

In certain examples, the time period for the individual stepwise increases may be set by the patient. In certain examples, the time period for the stepwise increase is set to a default value that may be configured based on, for example, the prescription information of the patient, the patient, characteristics of the patient (e.g., height, weight, etc. . . . ), the type of CPAP components being used, and the like.

Once the pressure level reaches the next set level, then display screen 326 may be displayed as is shown in FIG. 3C. Display screen 326 may include a note that most patients are asleep by the time the pressure is adjusted to this level (e.g., 8 cmH2O).

Display screen 328, like display screen 318 may include a prompt for increasing the pressure level to yet a further pressure level. Upon triggering the pressure increase, display screens 330, 332, 334 may be displayed to the patient. Display screen 336 may be displayed upon the pressure level reaching an indicated higher pressure level (e.g., 12 cmH2O). In certain examples, further pressure levels may be used and/or triggerable by the patient. In certain examples, additional notices may be displayed to the patient indicating that high pressure levels are infrequently (or never) used during treatment.

Finishing the test drive process may include instruction display screens that instruct the patient on how to undo the straps and remove the mask. In certain examples, a display screen that instructs the patient on operation of the various CPAP components, including flow generator 108, may be included. For example, a display screen may be shown that instructs the patient that therapy for CPAP treatment does not require the computing device 104 to operate and may be triggered via interacting with buttons or a control panel on the flow generator.

Figure 4:
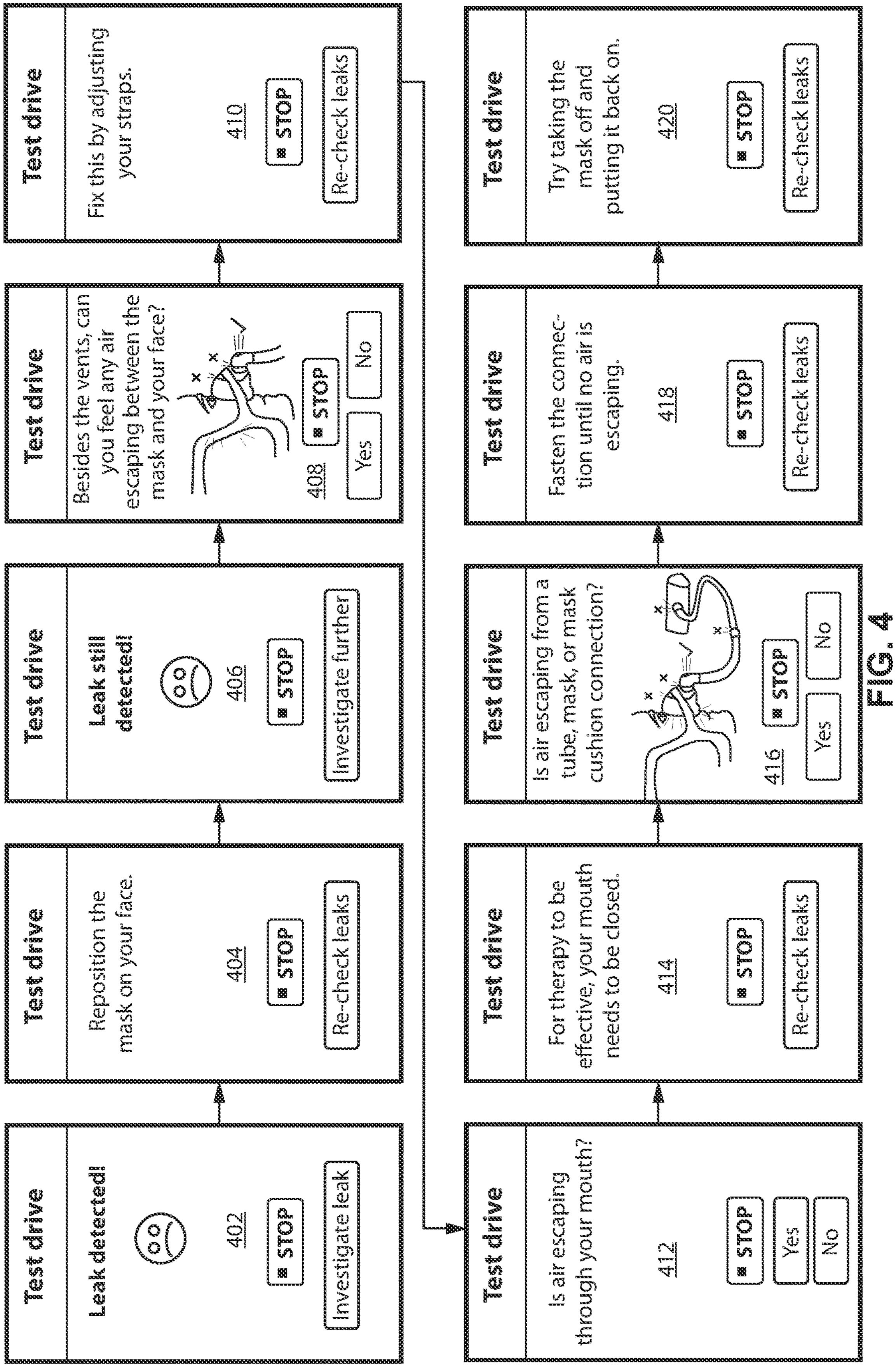
FIG. 4 shows a series of screens that assist a user in addressing a detected leak according to certain examples.

Description of FIG. 4

FIG. 4 shows a series of screens that assist a user in addressing a detected leak according to certain examples. As discussed above, a leak checking process may be conducted while any of the display screens in FIGS. 3A-3C are shown.

Display screen 402 is the first display screen that may be displayed upon detection of a leak. The display screen may include two buttons, one to investigate the leak and another to stop (e.g., to turn off the CPAP system).

It will be appreciated that the order in which the troubleshooting display screens are displayed (e.g., those shown in FIG. 4) may be configured based on various factors including, for example, the type of components being used, the patient, acquired sensor data, and other factors.

In any event, display screen 404 instructs the patient to reposition the mask on their face. Once the mask has been repositioned the patient may retrigger the leak check. If the leak is fixed, a display screen may be shown to patient informing them of such and the process may revert to the display screens shown in FIGS. 3A-3C (e.g., in which the leak was initially detected) and the test drive process may continue as discussed in those figures. If, however, a leak is still detected, then display screen 406 is presented. The patient may investigate the leak further via the button shown in display screen 406.

Display screen 408 includes an instructional image asking the patient to determine if air is escaping. The patient may select either Yes or No. If No is selected, then display screen 412 may be displayed (display screen 410 may be skipped). If Yes is selected, then display screen 410 is displayed with instructions for the patient to adjust the straps of the mask. The patient may then recheck for leaks. If a leak is still detected then 406 may be displayed again and the further investigative option may be shown at display screen 412.

Display screen 412 asks the patient to answer if air is escaping their mouth. If the patient answers No, then display screen 414 is skipped and display screen 416 is displayed. If the patient answers Yes, then display screen 414 is displayed with instructions to address this particular leak cause (e.g., instructing the user to close their mouth during therapy). If a leak is still present after rechecking in 414, then 406 is displayed again and the investigate further option triggers display screen 416.

Display screen 416 asks the patient to determine if air is escaping from the tube, mask, or mask cushion connection. An image or other visual representation of these components may be shown to the patient of the locations of possible escaping air. The nature of the visual representation may be based on the specific type of components that have been previously recognized. If the patient answers No in display screen 416, then display screen 420 may be displayed. If the patient answers Yes, then display screen 418 is displayed with instructions to fasten the connections. A patient may trigger the rechecking of the leak in 418. If a leak is still detected, then 406 may be displayed again, with the further investigative action being the display of display screen 420.

Display screen 420 instructs the patient to take the mask off and place it back on. The patient may then recheck for leaks.

Any of the display screens shown in FIG. 4 may include audio, video, animations, or pictures. Such media may help the patient in diagnosing a detected leak. As discussed above, the order in which the different investigative options (e.g., 404, 408, 412, 416) are presented may also be adjusted. In certain examples, the ordering may be based on characteristics of the patient and/or the types of components of the CPAP system that have been recognized.

In certain examples, the leak testing may include presenting the user with an image of their face (e.g., perhaps acquired with a camera of the user's computing device) with the mask on. Diagnosing the leak may include having the user indicate (e.g., via a touch screen or the like) where within the image air is escaping. Possible solutions may be shown to the user based on the location indicated by the user. In certain examples, a virtual avatar with a mask on may be displayed. The display of the avatar may allow the user to indicate where they are feeling the leak (e.g., by indicating a specific area, portion, or location on the mask). This type of approach may replace or supplement the successive images shown in FIG. 4.

Description of FIGS. 5A-5E

FIGS. 5A-5E are signal diagrams showing processing and communication performed by computing device 104, flow generator 108, and/or mask 110 according to certain examples. The processing shown in FIGS. 5A-5E may occur in conjunction with the display of any of the display screens discussed herein. In general, the processing discussed in FIGS. 5A-5E corresponds to the screens shown in FIGS. 3A-4.

At 502, the process begins when the test drive application (or process within an already running application) is started. For example, a patient may launch an app on their mobile phone for the test drive application. Alternatively, the patient may begin the test drive process from within an already running application on their mobile device. As discussed herein, the patient may have setup their mobile phone (or other computing device) to communicate with CPAP system 106 and/or components thereof. Such communication may allow computing device 104 to control functionality of CPAP system 106 (such as when positive air pressure is supplied and the pressure level it is supplied at).

At 504, prescription data is acquired. In certain examples, this data is loaded from local memory of the computing device 104. In certain examples, this data is acquired from a remote computing resource (e.g., a server or the like). The prescription data may be used to present informational displays at 506 that are contextually relevant to the patient to which the prescription data pertains. The presentation of such information may occur using animation, audio, video, images, text, or any combination thereof. The presentation may include a description of the test drive process and the role of each component in the patient CPAP system.

At 508, the patient may trigger a start command for the beginning of the test drive process (e.g., 306 in FIG. 3A). In response to the start command, at 510, the computing device 104 may transmit a wireless message to the flow generator 108. The wireless message may include an instruction to set the pressure level of the provided air pressure to "X." An initial example of X may be 4 $cmH_2O$.

The flow generator 108 may receive the instruction at 512 and set the pressure that is provided to X. If the flow generator has not already been started, the initial message from the computing device 104 may also include an instruction to start the flow generator 108. Air flow at pressure X may then be provided at 516 to the patient interface 110 and the patient wearing the patient interface 110. During this process of communicating with the flow generator, further informational displays may be shown at 514 (e.g., display screens 308, 310, and 312).

At 518 information displays concerning the pressure level being provided (e.g., 320, 322, and/or 324) from the flow generator 108 may be generated by the computing device 104 and display to the patient.

The informational displays may include an option to stop the flow generator. 520 occurs when such a stop command is triggered by the patient (e.g., by hitting a "Stop" button that is included in the display screens shown in FIGS. 3A-3C). Upon reception of the stop command, the computing device 104 may generate and send a wireless message to the flow generator 108. The flow generator 108 receives the message at 522 and responsively turns off at 522.

524 occurs when a leak check command is received. In certain examples, such a command is generated in response to user input (e.g., the user indicating that leaks should be checked). In certain examples, the leak command is automatically generated by the test drive application. For example, each time pressure is increased, the leak check command may be automatically triggered.

Figure 5A:
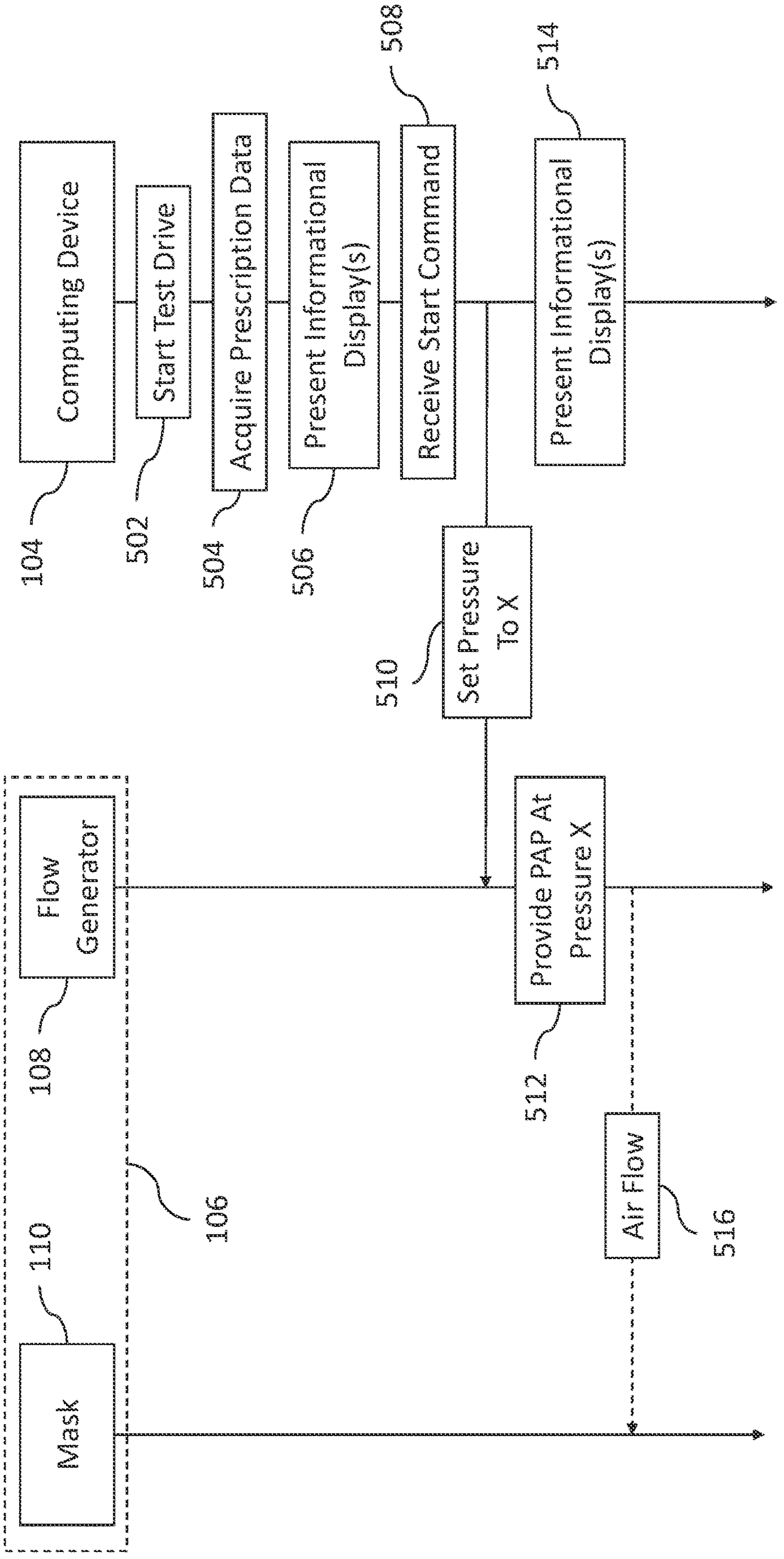
FIGS. 5A-5E are signal diagrams showing processing and communication performed by a mobile device, flow generator, and/or mask according to certain examples.
Figure 5B:
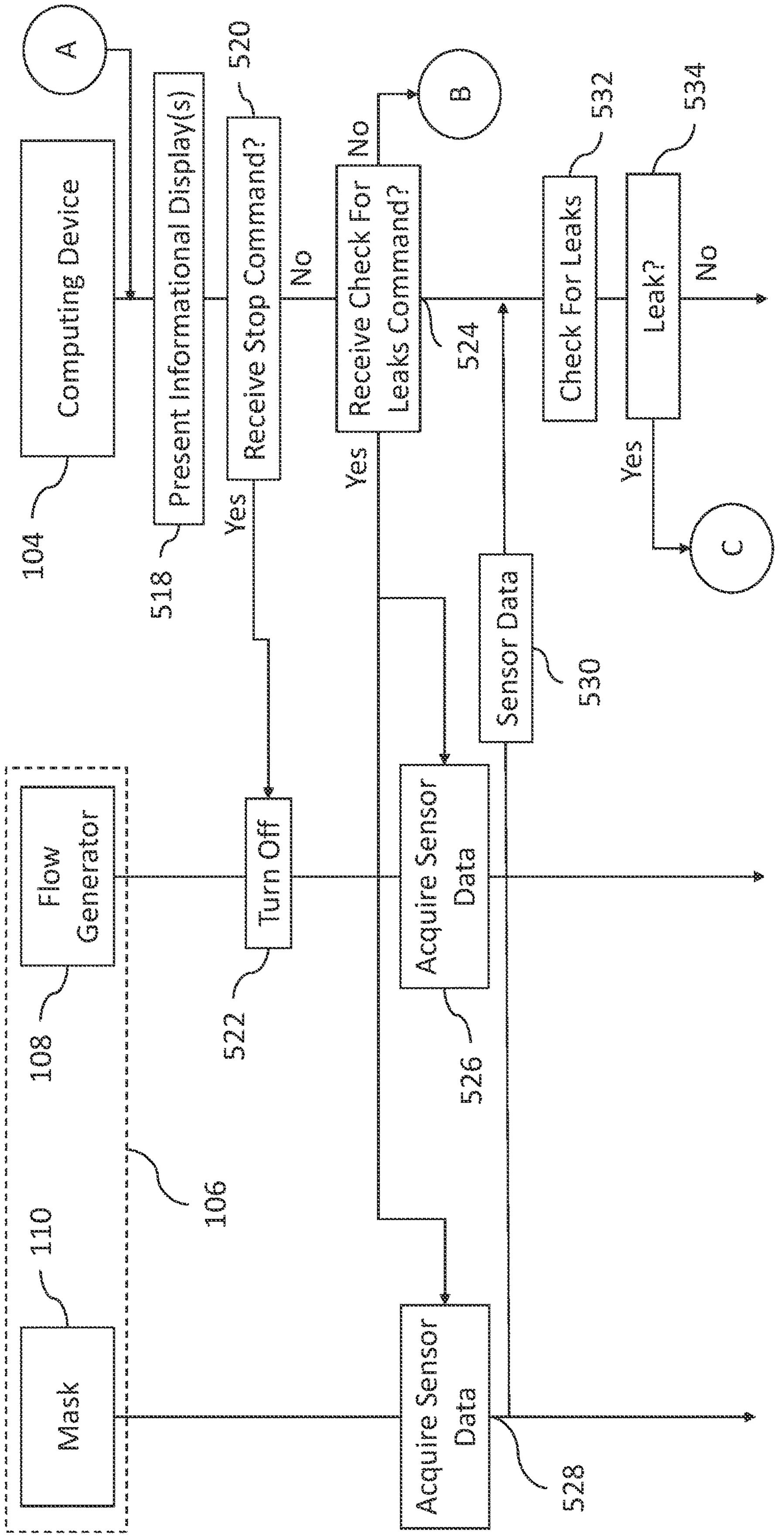
Figure 5C:
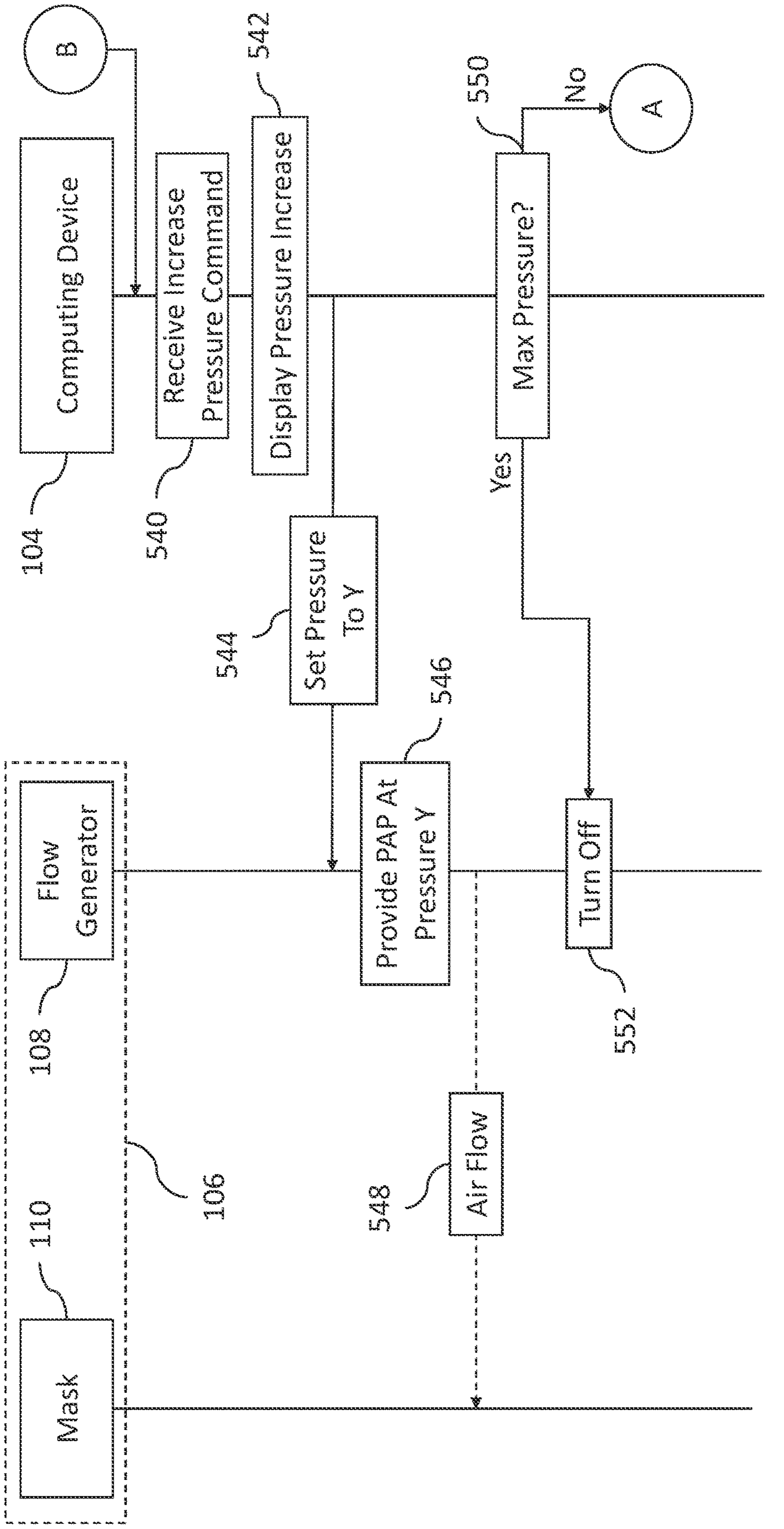

In any event, if no leak check command is triggered, then the process proceeds to B in FIG. 5C. However, if a leak check command is triggered, then the test drive process communicates with the CPAP system 106 to acquire sensor data. For example, the computing device 104 communicates with the flow generator 108 to acquire sensor data 526 (e.g., related to air flow at the outlet of the flow generator). The computing device 104 may also communicate with mask 110 to acquire sensor data 528 related to air flow that occurs at the mask (e.g., expiration flow that occurs via a vent in the mask 110). The sensor data is responsively communicated back to the computing device 104 at 530. In certain examples, the sensor data acquired from the mask 110 may be communicated back to the flow generator 108, which may then relay that data back to the computing device 104 (along with data acquired at 526). In certain examples, the sensor data include any data that measures a physical quantity, such as, for example, pressure, flow, humidity, acceleration, orientation, temperature, other quantity, and/or a combination thereof.

At 532, the computing device 104 may determine if a leak is present based on the acquire sensor data. At 534, if a leak is present the process proceeds to C in FIG. 5D. If no leak is detected, then the process proceeds to 540 in FIG. 5C. In certain examples, the determination of whether a leak is present may be made by the flow generator (e.g., based on the acquired sensor data). In such an instance, the flow generator (or other CPAP component) may send the leak determination result to the computing device 104 to be acted upon at 534. In certain examples, the sensor data transmitted from the CPAP system 106 may be transmitted to the computing device 104, which may then transmit such data to an external computing resource (e.g., a cloud-based computer system). The external computing resource may make the determination if a leak is present and send a message to the computing device 104 to be acted upon at 534.

Turning to FIG. 5C, at 540 a pressure increase command is triggered on the computing device 104. In certain examples, this may be in response to a patient manually triggering a pressure increase button. In certain examples, the requirement for manual triggering of a pressure increase by the user may provide them with an opportunity to become acclimated with a given pressure before proceeding to a higher pressure level. However, in certain examples, the pressure increase command is automatically provided.

At 542, the pressure increase may be displayed to the patient on the computing device or display associated therewith.

At 544, the computing device 104 generates a wireless data message that includes an instruction to increase the pressure that is to be provided by the CPAP system 106 to the patient to pressure Y (thus increasing the pressure from X to Y).

At 546, the flow generator 108 may receive the message and responsively increase the pressure (e.g., from 6 to 7 cmH2O) of the air flow 548 that is being provided to mask 110.

In certain examples, a max pressure level is checked at 550 and if the max pressure has been reached (e.g., for the test drive), then a wireless data message may be generated and sent to turn off the flow generator at 552. The process may then be stopped until the user restarts from 502. In certain examples, this check may be performed by checking if the pressure level is above a maximum authorized pressure level. In any event, if the max pressure has not been reached, then the process may return to A in FIG. 5B.

Figure 5D:
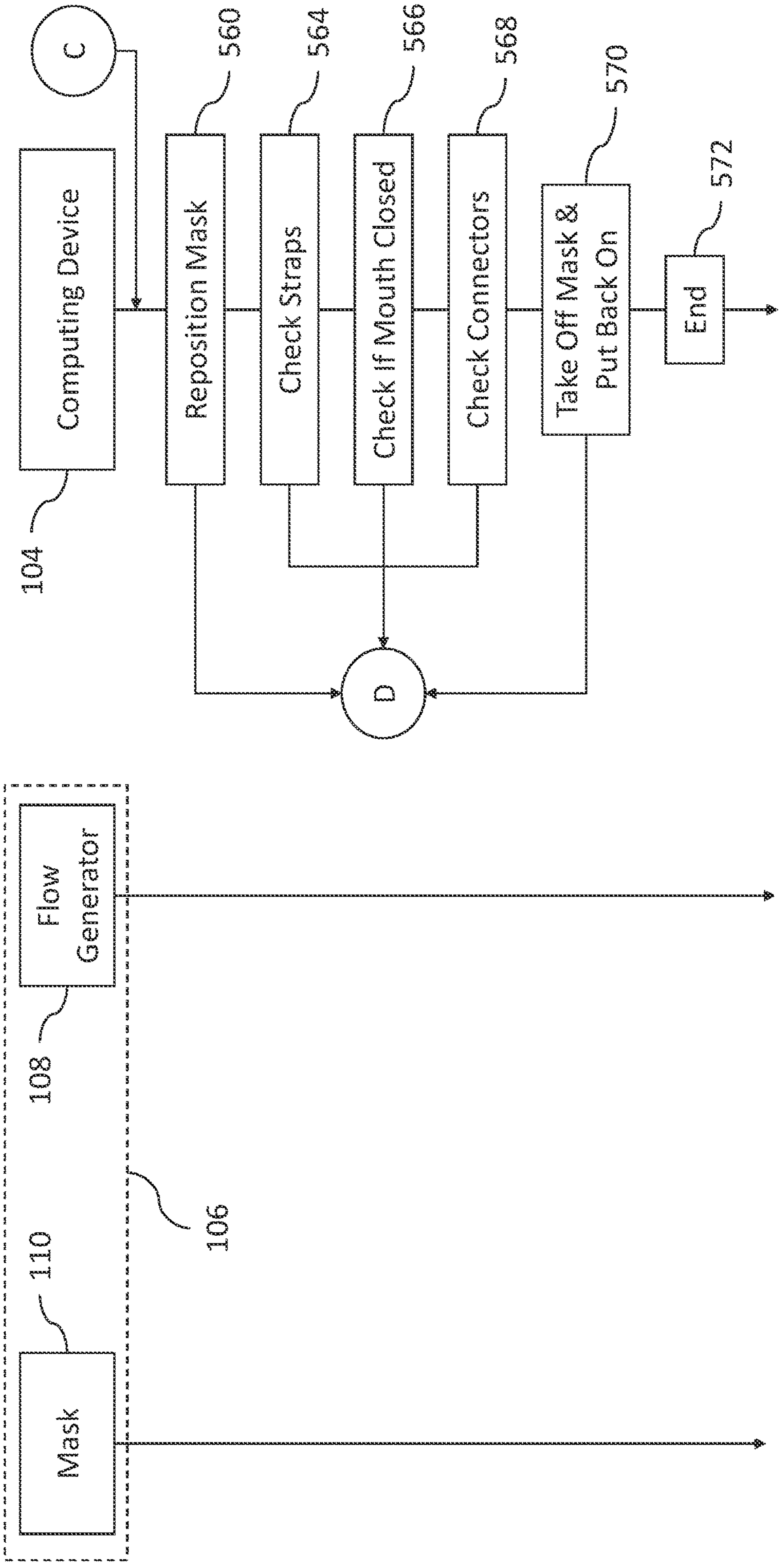

Turning to FIG. 5D, if a leak is detected at 534, then the process arrives at C in FIG. 5D. In certain examples, an instructional display may be generated and shown to the patient of the computing device regarding the presence of a leak.

FIG. 5D includes multiple different troubleshooting options 560, 564, 566, 568, 570 for attempting to address a detected leak. The order in which the troubleshooting options are selected by the computing device 104 and displayed to a user may occur in any order. In certain examples, a selected troubleshooting option may be based on the patient, the detected sensor data, the type of components of the CPAP system 106, and/or other factors. Thus, for example, 566 may be performed first, and if a leak is still detected, then 570, then 564, then 560, then 568, etc. Other orders are also possible—e.g., 560, then 564, then 566, then 568, then 570. In certain examples, the order is preset (or has a default order). In certain examples, a patient may choose which troubleshooting options to perform. Thus, a patient may show 564 first and if there is still a problem may then select from the remaining troubleshooting options.

Figure 5E:
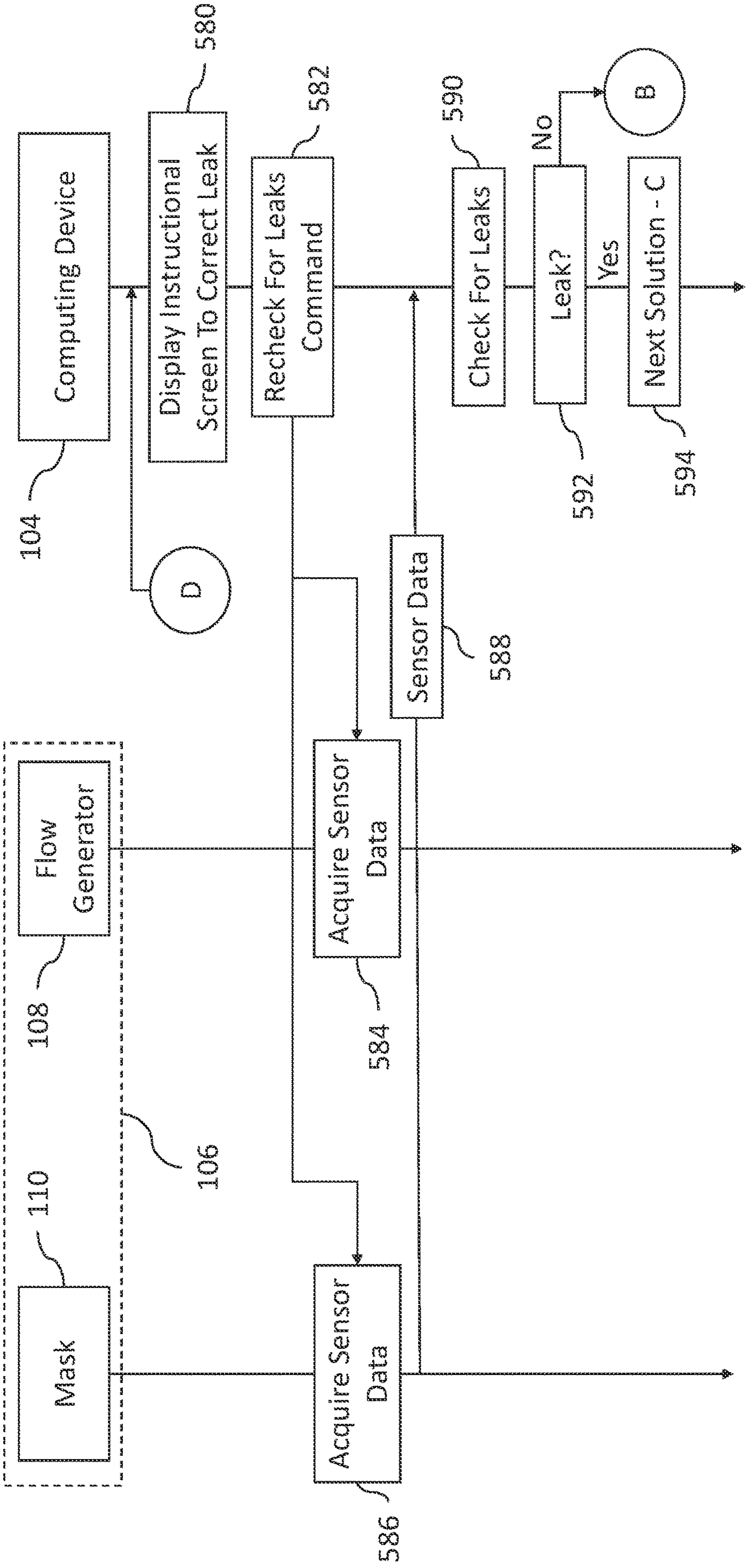

Selection of each troubleshooting option moves the process to D in FIG. 5E. If all of the trouble shooting options are exhausted then the leak process ends at 572.

At 580 in FIG. 5E, an instruction screen may be displayed according to the selected trouble shooting option. For example, display screens 412 and 414 may be displayed based on selection of the troubleshooting option 566.

Once the patient has proceeded through the display screens for the selected troubleshooting option, then a recheck leaks command may be triggered at 582. In certain examples, this may be a manual triggering by the patient (e.g., by hitting a button in a display screen). In other examples, the rechecking of leaks may be automatically triggered (e.g., after a predetermined period of time or the like). In any event, the recheck leaks command at 582 may cause the computing device 104 to communicate with the flow generator 108 and/or other components of the CPAP system 106 to acquire sensor data (e.g., similar to 524, 526, 528, and 530) at 584 and 586 that is returned to the computing device 104 at 588.

At 590, the computing device 104 may recheck for leaks based on sensor data acquired at 588. If no leak is determined at 592, then the process returns to B in FIG. 5C. If, however, there is a leak, then the process returns to C in FIG. 5D, selects the next troubleshooting option, and loops back around to recheck for leaks in FIG. 5E in accordance with the newly selected troubleshooting option.

In certain examples, the leak check process may also be aborted by having the patient stop the flow generator (e.g., via 520 in FIG. 5B).

In certain examples, the leak troubleshooting options that are available may be selected based on the type of the CPAP component (e.g., the type of mask) that is being used by the patient. Thus, for example, troubleshooting options that may be present with one mask type may not be present for another mask type. In certain examples, the order of the troubleshooting options may be adjusted based on the type of CPAP component that is being used by the patient. Accordingly, troubleshooting steps that are tailored to the components actually used may be generated and displayed to the patient. Such tailored troubleshooting options may facilitate increased success rates in correcting leaks. The order and/or presence of a particular troubleshooting option may be determined based on the CPAP component(s) being used, the prescription information for a patient, characteristics of the patient (e.g., height, weight, or other personal characteristics, etc. . . . ).

In certain examples the order and/or presence of a particular troubleshooting options may be updated based on the effectiveness of those options with other patients. Specifically, data for each use of a troubleshooting option may be stored or otherwise logged on a per patient basis. This information may be transmitted to a central database where analysis may be performed to determine which troubleshooting options are effective (or more likely to solve a given leak). Such a process may then allow the troubleshooting process to be dynamically updated as new data is acquired. The determination of the effectiveness of a troubleshooting option may be based on the type of CPAP component(s) being used by a patient, or characteristics of the patients.

In certain examples, selection of a troubleshooting option may be based on sensor data from one or more CPAP components. For example, certain troubleshooting options may be more effective for leaks found at higher pressure levels than leaks found at lower pressure levels.

Thus, for example, the selection of what troubleshooting option to pursue may be based on: 1) the type of mask (or other CPAP component), 2) acquired sensor data for a CPAP component (e.g., the mask), 3) user input (e.g., having the user indicate where air is escaping, and the like.

Description of FIG. 6

FIG. 6 is a block diagram of an example computing device 600 (which may also be referred to, for example, as a "computing device," "computer system," or "computing system") herein. In certain examples, the computing device 600 includes one or more of the following: a processing system 602, which includes one or more hardware processors (e.g., central processing units or CPUs); one or more memory devices 606; one or more network interface devices 618; one or more display interfaces 614; and one or more user input adapters 610. Elements of computing device 600 may communicate with one another via system bus 604. Additionally, in some examples, the computing device 600 is connected to or includes a display device 616, user input device 612, database 620, and/or external resources 622 (which may be another instance of computing device 600). As will be explained below, these elements (e.g., the processing system 602, memory devices 606, network interface devices 618, display interfaces 614, user input adapters 610, display device 616) are hardware devices (for example, electronic circuits or combinations of circuits) that are configured to perform various different functions for the computing device 600.

In some examples, each or any of the processors (e.g., CPUs 1, 2, 3, or 4) of the processing system 602 is or includes, for example, a single- or multi-core processor, a microprocessor (e.g., which may be referred to as a central processing unit or CPU), a digital signal processor (DSP), a microprocessor in association with a DSP core, an Application Specific Integrated Circuit (ASIC), a Field Programmable Gate Array (FPGA) circuit, and/or a system-on-a-chip (SOC) (e.g., an integrated circuit that includes a CPU and other hardware components such as memory, networking interfaces, and the like). In certain examples, each or any of the processors may use an instruction set architecture such as x86 or Advanced RISC Machine (ARM).

In some examples, each or any of the memory devices 606 is or includes a random access memory (RAM) (such as a Dynamic RAM (DRAM) or Static RAM (SRAM)), a flash memory (based on, e.g., NAND or NOR technology), a hard disk, a magneto-optical medium, an optical medium, cache memory, a register (e.g., that holds instructions), or other type of device that performs the volatile or non-volatile storage of data and/or instructions (e.g., software that is executed on or by processors of the processing system 602). Memory devices 606 are examples of non-transitory computer-readable storage media.

In some examples, each or any of the network interface devices 618 includes one or more circuits (such as a baseband processor and/or a wired or wireless transceiver), and implements layer one, layer two, and/or higher layers for one or more wired communications technologies (such as Ethernet (IEEE 802.3)) and/or wireless communications technologies (such as Bluetooth, WiFi (IEEE 802.11), GSM, CDMA2000, UMTS, LTE, LTE-Advanced (LTE-A), and/or other short-range, mid-range, and/or long-range wireless communications technologies). Transceivers may comprise circuitry for a transmitter and a receiver. The transmitter and receiver may share a common housing and may share some or all of the circuitry in the housing to perform transmission and reception. In some examples, the transmitter and receiver of a transceiver may not share any common circuitry and/or may be in the same or separate housings.

In some examples, each or any of display interface 614 is or includes one or more circuits that: receive data from the processors of the processing system 602, generate (e.g., via a discrete GPU, an integrated GPU, a CPU executing graphical processing, or the like) corresponding image data based on the received data, and/or output (e.g., a High-Definition Multimedia Interface (HDMI), a DisplayPort Interface, a Video Graphics Array (VGA) interface, a Digital Video Interface (DVI), or the like), the generated image data to the display device 616, which displays the image data. Alternatively, or additionally, in some examples, each or any of the display interfaces 614 is or includes, for example, a video card, video adapter, or graphics processing unit (GPU).

In some examples, each or any of user input adapter 610 is or includes one or more circuits that receive and process user input data from one or more user input devices 612 that are included in, attached to, or otherwise in communication with the computing device 600, and that output data based on the received input data to the processors 602. Alternatively, or additionally, in some examples each or any of the user input adapters 610 is or includes, for example, a PS/2 interface, a USB interface, a touchscreen controller, or the like; and/or the user input adapters 610 facilitates input from user input devices 612, which may include, for example, a keyboard, mouse, trackpad, touchscreen, voice input, etc. In certain examples, user input adapter 610 may be configured to process data from other types of input sources that are not from a user. For example, user input adapter 610 (e.g., an input adapter) may process data from one or more sensors (e.g., flow, pressure, temperature, or other types of sensors).

In some examples, the display device 616 may be a Liquid Crystal Display (LCD) display, Light Emitting Diode (LED) display, or other type of display device. In examples where the display device 616 is a component of the computing device 600 (e.g., the computing device and the display device are included in a unified housing of, for example, a mobile or tablet device), the display device 616 may be a touchscreen display (e.g., using capacitive or resistive technology to sense a touch) or non-touchscreen display. In examples where the display device 616 is connected to the computing device 600 (e.g., is external to the computing device 600 and communicates with the computing device 600 via a wire and/or via wireless communication technology), the display device 616 is, for example, an external monitor, projector, television, display screen, etc.

In various examples, the computing device 600 includes one, or two, or three, four, or more of each or any of the above-mentioned elements (e.g., the processing system 602, CPUs 1, 2, 3, or 4, memory devices 606, network interface devices 618, display interfaces 6514, and user input adapters 610). In some examples, the computing device 600 includes one or more of: a processing system 602 that includes hardware processors (e.g., CPUs 1, 2, 3, and/or 4); a memory or storage system that includes the memory devices; and a network interface system that includes the network interface devices 618.

The computing device 600 may be arranged, in various examples, in many different ways. As just one example, the computing device 600 may be arranged such that the processors include: a multi (or single)-core processor; a first network interface device (which implements, for example, WiFi, Bluetooth, NFC, etc.); a second network interface device that implements one or more cellular communication technologies (e.g., 3G, 4G LTE, CDMA, etc. . . . ); memory or storage devices (e.g., RAM, flash memory, or a hard disk). The processor, the first network interface device, the second network interface device, and the memory devices may be integrated as part of the same SOC (e.g., one integrated circuit chip). As another example, the computing device 600 may be arranged such that: the processors include two, three, four, five, or more multi-core processors; the network interface devices 618 include a first network interface device that implements Ethernet and a second network interface device that implements WiFi and/or Bluetooth; and the memory devices 606 may include RAM and storage in the form of flash memory or hard disk.

As previously noted, whenever it is described in this document that a software module or software process performs any action, the action is in actuality performed by underlying hardware elements according to the instructions that comprise the software or software module.

The hardware configurations shown in FIG. 6 and described above are provided as examples, and the subject matter described herein may be utilized in conjunction with a variety of different hardware architectures and elements. For example: in many of the Figures in this document, individual functional/action blocks are shown; in various examples, the functions of those blocks may be implemented using (a) individual hardware circuits, (b) using an application specific integrated circuit (ASIC) specifically configured to perform the described functions/actions, (c) using one or more digital signal processors (DSPs) specifically configured to perform the described functions/actions, (d) using the hardware configuration described above with reference to FIG. 6, (e) via other hardware arrangements, architectures, and configurations, and/or via combinations of the technology described in (a) through (e).

In certain examples, the techniques herein provide for increased patient acclimatization to therapy. Such increased acclimatization may be based on providing patients with increased control and tailored information notices upon first use. In certain examples, the techniques herein allow for increased patient comfort in using medical devices in their home without the need of a medical expert to set up and instruct on device usage In certain examples, a test drive CPAP therapy is provided that allows for a patient to control therapy aspects from their own mobile phone (or other computing device). The therapy may start out low and allow a patient to control when pressure is increased (e.g., the patient may increase pressure at their own pace).

In certain examples, tailored troubleshooting options may be presented that are generated based on a specific type of CPAP component(s) that have been detected.

Whenever it is described in this document that a given item is present in "some embodiments," "various embodiments," "certain embodiments," "certain example embodiments, "some example embodiments," "an exemplary embodiment," "certain examples," "some examples," or whenever any other similar language is used, it should be understood that the given item is present in at least one embodiment or example, though is not necessarily present in all embodiments or examples. Consistent with the foregoing, whenever it is described in this document that an action "may," "can," or "could" be performed, that a feature, element, or component "may," "can," or "could" be included in or is applicable to a given context, that a given item "may," "can," or "could" possess a given attribute, or whenever any similar phrase involving the term "may," "can," or "could" is used, it should be understood that the given action, feature, element, component, attribute, etc. is present in at least one example or embodiment, though is not necessarily present in all embodiments or examples. Terms and phrases used in this document, and variations thereof, unless otherwise expressly stated, should be construed as open-ended rather than limiting. As examples of the foregoing: "and/or" includes any and all combinations of one or more of the associated listed items (e.g., a and/or b means a, b, or a and b); the singular forms "a", "an" and "the" should be read as meaning "at least one," "one or more," or the like; the term "example" is used to provide examples of the subject under discussion, not an exhaustive or limiting list thereof; the terms "comprise" and "include" (and other conjugations and other variations thereof) specify the presence of the associated listed items but do not preclude the presence or addition of one or more other items; and if an item is described as "optional," such description should not be understood to indicate that other items are also not optional.

As used herein, the term "non-transitory computer-readable storage medium" includes a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVD, or Blu-Ray Disc, or other type of device for non-transitory electronic data storage. The term "non-transitory computer-readable storage medium" does not include a transitory, propagating electromagnetic signal.

While certain examples are described in connection with CPAP systems, it will be appreciated that the techniques herein may be applicable to other types of home medical equipment.

Although process steps, algorithms or the like, may be described or claimed in a particular sequential order, such processes may be configured to work in different orders. In other words, any sequence or order of steps that may be explicitly described or claimed in this document does not necessarily indicate a requirement that the steps be performed in that order; rather, the steps of processes described herein may be performed in any order possible. Further, some steps may be performed simultaneously (or in parallel) despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary, and does not imply that the illustrated process is preferred.

Although various embodiments and examples have been shown and described in detail, the claims are not limited to any particular embodiment or example. None of the above description should be read as implying that any particular element, step, range, or function is essential. All structural and functional equivalents to the elements of the above-described embodiments and examples that are known to those of ordinary skill in the art are expressly incorporated herein by reference and are intended to be encompassed. Moreover, it is not necessary for a device or method to address each and every problem sought to be solved by the present invention, for it to be encompassed by the invention.

No embodiment, example, feature, element, component, or step in this document is intended to be dedicated to the public.

The invention claimed is:

1. A non-transitory computer readable storage medium storing instructions for use with a computing device, which includes at least one hardware processor, that is configured to communicate with a respiratory therapy device of a continuous positive air pressure (CPAP) system, the respiratory therapy device configured to generate a supply of breathable gas delivered to a patient via a patient interface that is configured to engage with at least one airway of the patient, the stored instructions comprising instructions that are configured to cause the at least one hardware processor to perform operations comprising:

dynamically determining, based on a type of CPAP system and/or use of the CPAP system, a series of linked instruction displays to guide a user in setting up the CPAP system and/or the use of the CPAP system;

presenting, on a display device that is coupled to the computing device and as part of the dynamically determined series of linked instruction displays, a display associated with increasing towards a target pressure level for the supply of breathable gas that is to be provided to the patient;

presenting, on the display device and based on a leak determination in connection with a provision of the supply of breathable gas, a display that indicates a leak has been detected;

selecting, from among a plurality of troubleshooting options, a first troubleshooting option to present to the user that is based on the type of CPAP system;

in connection with the leak determination and holding of the supply of breathable gas at a held pressure level that is different from the target pressure level, presenting, as part of the series of linked instruction displays, a display that includes instructions for at least the selected first troubleshooting option that is selected to correct a leak;

subsequent to display of the selected first troubleshooting option and based on another leak determination that a leak is still detected, presenting, as part of the series of linked instruction displays, a second troubleshooting option to the user; and subsequent to display of the selected first troubleshooting option and based on another leak determination that a leak is no longer detected, presenting, as part of the series of linked instruction displays, a display that indicates the pressure of the supply of breathable gas is increasing towards the target pressure level.

2. The non-transitory computer readable storage medium of claim 1, wherein the supply of breathable gas is held at the held pressure level when the leak is still detected.

3. The non-transitory computer readable storage medium of claim 1, wherein the operations further comprise:

selecting the second troubleshooting option, from among the plurality of troubleshooting options, based in on the type of CPAP system.

4. The non-transitory computer readable storage medium of claim 1, wherein the operations further comprise:

in connection with increasing pressure of the supply of breathable gas, displaying incremental pressure changes based on increase in the pressure.

5. The non-transitory computer readable storage medium of claim 1, wherein the operations further comprise:

presenting, on the display device, a leak check display screen that indicates that a leak check process is being performed in association with the provision of the supply of breathable gas.

6. The non-transitory computer readable storage medium of claim 1, wherein increase of the pressure at which the supply of breathable gas is to be provided is based on receiving a user input from the user.

7. The non-transitory computer readable storage medium of claim 1, wherein increase of the pressure at which the supply of breathable gas is to be provided is automatically performed without an express user input from the user.

8. The non-transitory computer readable storage medium of claim 1, wherein the operations further comprise:

based on processing a pause instruction from the user, causing a pressure increase process for the supply of breathable gas to be paused.

9. The non-transitory computer readable storage medium of claim 1, wherein an order in which troubleshooting options are selected from the plurality of trouble shooting options is based at least in part on characteristics of the user and/or component types included in the CPAP system.

10. The non-transitory computer readable storage medium of claim 1, wherein at least one of the first and second troubleshooting options is selected based on sensed data, a type of patient interface, a type of respiratory therapy device, and/or characteristics of the user using the CPAP system.

11. The non-transitory computer readable storage medium of claim 1, wherein selection of at least one of the plurality of troubleshooting options is further based on an effectiveness metric that is dynamically updated based on effectiveness of the corresponding troubleshooting option.

12. The non-transitory computer readable storage medium of claim 1, wherein the operations further comprise:

receiving, from the respiratory therapy device, sensor data that is based on the supply of breathable gas delivered to the patient; and executing, using the sensor data, a leak detection process to determine whether a leak is represented in the supply of breathable gas delivered to the patient.

13. The non-transitory computer readable storage medium of claim 1, wherein the held pressure level is a pressure that is based on when the leak was detected.

14. The non-transitory computer readable storage medium of claim 1, wherein the operations further comprise:

acquiring a patient interface type for the patient interface that is being used; and acquiring a respiratory therapy device type for the respiratory therapy device that is being used, wherein the type of CPAP system is based on the acquired respiratory therapy device type and/or the patient interface type.

15. A method implemented on a computing system for guiding a user in setting up and/or using a CPAP system, the CPAP system comprising a respiratory therapy device configured to generate a supply of breathable gas delivered to a patient via a patient interface that is configured to engage with at least one airway of the patient, the method comprising:

dynamically determining, based on a type of CPAP system and/or use of the CPAP system, a series of linked instruction displays to guide a user in setting up the CPAP system and/or the use of the CPAP system;

presenting, on a display device that is coupled to the computing system and as part of the dynamically determined series of linked instruction displays, a display that is associated with increasing towards a target pressure level for the supply of breathable gas that is to be provided to the patient;

presenting, on the display device and based on a leak determination in connection with a provision of the supply of breathable gas, a display that indicates a leak has been detected;

selecting, from among a plurality of troubleshooting options, a first troubleshooting option to present to the user that is based on the type of CPAP system;

in connection with the leak determination and holding of the supply of breathable gas at a held pressure level that is different from the target pressure level, presenting, as part of the series of linked instruction displays, a display that includes instructions for at least the selected first troubleshooting option that is selected to correct a leak;

subsequent to display of the selected first troubleshooting option and based on another leak determination that a leak is still detected, presenting, as part of the series of linked instruction displays, a second troubleshooting option to the user; and subsequent to display of the selected first troubleshooting option and based on another leak determination that a leak is no longer detected, presenting, as part of the series of linked instruction displays, a display that indicates the pressure of the supply of breathable gas is increasing towards the target pressure level.

16. The method of claim 15, wherein the supply of breathable gas is held at the held pressure level when the leak is detected.

17. The method of claim 15, further comprising:

presenting, on the display device, a leak check display screen that indicates that a leak check process is being performed in association with the provision of the supply of breathable gas.

18. The method of claim 15, wherein at least one of the first and second troubleshooting options is selected based on sensed data, a type of patient interface, a type of respiratory therapy device, and/or characteristics of the user using the CPAP system.

19. The method of claim 15, wherein an order in which troubleshooting options are selected from the plurality of troubleshooting options is based at least in part on characteristics of the user and/or component types included in the CPAP system.

20. A computing device for communicating with a continuous positive air pressure (CPAP) system that includes (a) a respiratory therapy device that is configured to generate a supply of breathable gas that is delivered to a patient via a patient interface that is configured to engage with at least one airway of the patient, and (b) at least one sensor that is configured to measure a physical quantity while the breathable gas is supplied to the patient, the computing device comprising:

a display screen;

a wireless transceiver;

a processing system that includes at least one hardware processor and computer instructions comprising instructions that, when executed by at least one hardware processor, cause the at least one hardware processor to perform operations comprising:

dynamically determining, based on a type of CPAP system and/or use of the CPAP system, a series of linked instruction displays to guide a user in setting up the CPAP system and/or the use of the CPAP system;

presenting, on a display device that is coupled to the computing device and as part of the dynamically determined series of linked instruction displays, a display that is associated with increasing towards a target pressure level for the supply of breathable gas that is to be provided to the patient;

presenting, on the display device and based on a leak determination in connection with a provision of the supply of breathable gas, a display that indicates a leak has been detected;

selecting, from among a plurality of troubleshooting options, a first troubleshooting option to present to the user that is based on the type of CPAP system;

in connection with the leak determination and holding of the supply of breathable gas at a held pressure level that is different from the target pressure level, presenting, as part of the series of linked instruction displays, a display that includes instructions for at least the selected first troubleshooting option that is selected to correct a leak;

subsequent to display of the selected first troubleshooting option and based on another leak determination that a leak is still detected, presenting, as part of the series of linked instruction displays, a second troubleshooting option to the user; and subsequent to display of the selected first troubleshooting option and based on another leak determination that a leak is no longer detected, presenting, as part of the series of linked instruction displays, a display that indicates the pressure of the supply of breathable gas is increasing towards the target pressure level.

* * * * *